(12) United States Patent
Paul

(10) Patent No.: US 7,204,837 B2
(45) Date of Patent: Apr. 17, 2007

(54) SPINAL PLATE ASSEMBLY

(76) Inventor: Kamaljit S. Paul, 3220 Old Orchard La., Oshkosh, WI (US) 54902

( * ) Notice: Subject to any disclaimer, the term of this patent is extended or adjusted under 35 U.S.C. 154(b) by 320 days.

(21) Appl. No.: 10/627,065

(22) Filed: Jul. 24, 2003

(65) Prior Publication Data

US 2004/0153069 A1 Aug. 5, 2004

Related U.S. Application Data

(63) Continuation-in-part of application No. 10/202,705, filed on Jul. 24, 2002, now Pat. No. 7,070,599, which is a continuation-in-part of application No. 10/014,409, filed on Dec. 14, 2001, now Pat. No. 6,755,833.

(51) Int. Cl.
*A61B 17/58* (2006.01)

(52) U.S. Cl. .......................... 606/61; 606/69

(58) Field of Classification Search .............. 606/61, 606/69–73
See application file for complete search history.

(56) References Cited

U.S. PATENT DOCUMENTS

| | | |
|---|---|---|
| 2,406,832 A | 9/1946 | Hardinge |
| 2,486,303 A | 10/1949 | Longfellow |
| 2,580,821 A | 1/1952 | Nicola |
| 2,780,223 A | 2/1957 | Haggland |
| 3,244,170 A | 4/1966 | McElvenny |
| 3,534,731 A | 10/1970 | Muller |
| 3,596,656 A | 8/1971 | Kaute |
| 3,659,595 A | 5/1972 | Haboush |
| 3,695,259 A | 10/1972 | Yost |
| 3,741,205 A | 6/1973 | Markolf et al. |

(Continued)

FOREIGN PATENT DOCUMENTS

DE 251246 9/1912

(Continued)

OTHER PUBLICATIONS

"Blackstone™ Anterior Cervical Plate," Blackstone Medical Inc., Product literature, date unknown, 4 sheets.

(Continued)

*Primary Examiner*—Eduardo C. Robert
*Assistant Examiner*—Annette Reimers
(74) *Attorney, Agent, or Firm*—Wilhelm Law Service, S.C.; Thomas D. Wilhelm

(57) ABSTRACT

Spinal plate assemblies, methods of fabrication, and methods of use. Such assemblies comprises blocking structures assembled to spinal plates. The blocking structure comprises an elongate band which can be against structure of the plate. The band is mounted into a continuous or intermittent channel in the plate, and extends into an aperture in the plate. The band responds to side forces applied by interfering elements of bone fasteners driven through an aperture, by moving away from the interfering element, and returning to a blocking position over the interfering element after the interfering element has passed the band. Methods of fabrication include inserting the blocking structure, optionally longitudinally, into the channel. Methods of use include advancing bone screws through an aperture and past the band. The bone screw deflects the band as the screw passes, and the band moves to the blocking position when the screw has moved past the band.

82 Claims, 5 Drawing Sheets

U.S. PATENT DOCUMENTS

| | | |
|---|---|---|
| RE28,841 E | 6/1976 | Allgower et al. |
| 4,246,660 A | 1/1981 | Wevers |
| 4,388,921 A | 6/1983 | Sutter et al. |
| RE31,628 E | 7/1984 | Allgower et al. |
| 4,484,570 A | 11/1984 | Sutter et al. |
| 4,488,543 A | 12/1984 | Tornier |
| 4,503,848 A | 3/1985 | Caspar et al. |
| 4,513,744 A | 4/1985 | Klaue |
| 4,794,918 A | 1/1989 | Wolter |
| 4,943,292 A | 7/1990 | Foux |
| 4,955,908 A | 9/1990 | Frey et al. |
| 4,957,497 A | 9/1990 | Hoogland et al. |
| 5,085,660 A | 2/1992 | Lin |
| 5,108,395 A | 4/1992 | Laurain |
| 5,113,685 A | 5/1992 | Asher et al. |
| 5,129,903 A | 7/1992 | Luhr et al. |
| 5,147,360 A | 9/1992 | Dubousset |
| 5,147,361 A | 9/1992 | Ojima et al. |
| 5,180,381 A | 1/1993 | Aust et al. |
| 5,234,431 A | 8/1993 | Keller |
| 5,261,910 A | 11/1993 | Warden et al. |
| 5,324,290 A | 6/1994 | Zdeblick et al. |
| 5,344,421 A | 9/1994 | Crook |
| 5,364,399 A | 11/1994 | Lowery et al. |
| 5,423,826 A | 6/1995 | Coates et al. |
| 5,478,342 A | 12/1995 | Kohrs |
| 5,486,176 A | 1/1996 | Hildebrand et al. |
| 5,520,690 A | 5/1996 | Errico et al. |
| 5,520,696 A | 5/1996 | Wenstrom, Jr. |
| 5,527,311 A | 6/1996 | Procter et al. |
| 5,531,746 A | 7/1996 | Errico et al. |
| 5,534,032 A | 7/1996 | Hodorek |
| 5,549,612 A | 8/1996 | Yapp et al. |
| 5,569,247 A | 10/1996 | Morrison |
| 5,569,251 A | 10/1996 | Baker et al. |
| 5,578,034 A * | 11/1996 | Estes ............................ 606/61 |
| 5,601,553 A | 2/1997 | Trebing et al. |
| 5,603,713 A | 2/1997 | Aust et al. |
| 5,607,426 A | 3/1997 | Ralph et al. |
| 5,607,428 A | 3/1997 | Lin |
| 5,616,142 A | 4/1997 | Yuan et al. |
| 5,616,144 A | 4/1997 | Yapp et al. |
| 5,620,443 A | 4/1997 | Gertzbein et al. |
| 5,643,265 A | 7/1997 | Errico et al. |
| 5,653,708 A | 8/1997 | Howland |
| 5,676,666 A | 10/1997 | Oxland et al. |
| 5,676,703 A | 10/1997 | Gelbard |
| 5,681,311 A | 10/1997 | Foley et al. |
| 5,709,686 A | 1/1998 | Talos et al. |
| 5,713,900 A | 2/1998 | Benzel et al. |
| 5,725,588 A | 3/1998 | Errico et al. |
| 5,728,127 A | 3/1998 | Asher et al. |
| 5,735,853 A | 4/1998 | Olerud |
| 5,735,899 A | 4/1998 | Schwartz et al. |
| 5,741,258 A | 4/1998 | Klaue et al. |
| 5,797,912 A | 8/1998 | Runciman et al. |
| 5,810,823 A | 9/1998 | Klaue et al. |
| 5,876,402 A | 3/1999 | Errico et al. |
| 5,879,389 A | 3/1999 | Koshino |
| 5,904,683 A * | 5/1999 | Pohndorf et al. ............ 606/61 |
| 5,951,558 A | 9/1999 | Fiz |
| 5,954,722 A * | 9/1999 | Bono ............................ 606/61 |
| 5,964,762 A | 10/1999 | Biedermann et al. |
| 5,976,141 A | 11/1999 | Haag et al. |
| 6,017,345 A | 1/2000 | Richelsoph |
| 6,022,350 A | 2/2000 | Ganem |
| 6,030,389 A | 2/2000 | Wagner et al. |
| 6,039,740 A | 3/2000 | Olerud |
| 6,106,557 A | 8/2000 | Robioneck et al. |
| 6,117,173 A | 9/2000 | Taddia et al. |
| 6,129,730 A | 10/2000 | Bono et al. |
| 6,139,550 A | 10/2000 | Michelson |
| 6,152,927 A * | 11/2000 | Farris et al. ................ 606/69 |
| 6,159,213 A | 12/2000 | Rogozinski |
| 6,193,721 B1 | 2/2001 | Michelson |
| 6,206,882 B1 | 3/2001 | Cohen |
| 6,214,005 B1 | 4/2001 | Benzel et al. |
| 6,224,602 B1 * | 5/2001 | Hayes ........................ 606/69 |
| 6,228,085 B1 | 5/2001 | Theken et al. |
| 6,235,033 B1 | 5/2001 | Brace et al. |
| 6,235,034 B1 | 5/2001 | Bray |
| 6,238,396 B1 | 5/2001 | Lombardo |
| 6,241,731 B1 | 6/2001 | Fiz |
| 6,254,603 B1 | 7/2001 | Gertzbein et al. |
| 6,258,089 B1 | 7/2001 | Campbell et al. |
| 6,261,291 B1 | 7/2001 | Talaber et al. |
| 6,273,889 B1 | 8/2001 | Richelsoph |
| 6,293,949 B1 | 9/2001 | Justis et al. |
| D449,692 S | 10/2001 | Michelson |
| 6,306,136 B1 | 10/2001 | Baccelli |
| 6,306,139 B1 | 10/2001 | Fuentes |
| 6,322,562 B1 | 11/2001 | Wolter |
| 6,328,738 B1 | 12/2001 | Suddaby |
| 6,331,179 B1 | 12/2001 | Freid et al. |
| 6,332,887 B1 | 12/2001 | Knox |
| 6,342,055 B1 | 1/2002 | Eisermann et al. |
| 6,361,537 B1 | 3/2002 | Anderson |
| 6,364,881 B1 | 4/2002 | Apgar et al. |
| 6,383,186 B1 | 5/2002 | Michelson |
| 6,398,783 B1 | 6/2002 | Michelson |
| 6,402,755 B1 | 6/2002 | Pisharodi |
| 6,402,756 B1 | 6/2002 | Ralph et al. |
| 6,406,478 B1 | 6/2002 | Kuo |
| 6,413,259 B1 | 7/2002 | Lyons et al. |
| 6,416,528 B1 | 7/2002 | Michelson |
| 6,428,542 B1 | 8/2002 | Michelson |
| 6,454,769 B2 | 9/2002 | Wagner et al. |
| 6,454,771 B1 | 9/2002 | Michelson |
| 6,458,133 B1 | 10/2002 | Lin |
| 6,478,797 B1 | 11/2002 | Paul |
| 6,503,250 B2 | 1/2003 | Paul |
| 6,527,776 B1 | 3/2003 | Michelson |
| 6,533,786 B1 * | 3/2003 | Needham et al. ............ 606/61 |
| 6,572,619 B2 | 6/2003 | Santilli |
| 6,575,975 B2 | 6/2003 | Brace et al. |
| 6,579,290 B1 | 6/2003 | Hardcastle et al. |
| 6,592,586 B1 | 7/2003 | Michelson |
| 6,595,993 B2 | 7/2003 | Donno et al. |
| 6,599,290 B2 | 7/2003 | Bailey et al. |
| 6,602,255 B1 * | 8/2003 | Campbell et al. ............ 606/69 |
| 6,602,256 B1 * | 8/2003 | Hayes ........................ 606/69 |
| 6,602,257 B1 | 8/2003 | Thramann |
| 6,605,090 B1 | 8/2003 | Trieu et al. |
| 6,613,053 B1 | 9/2003 | Collins et al. |
| 6,616,666 B1 | 9/2003 | Michelson |
| 6,620,163 B1 | 9/2003 | Michelson |
| 6,623,486 B1 | 9/2003 | Weaver et al. |
| 6,626,907 B2 | 9/2003 | Campbell et al. |
| 6,652,525 B1 * | 11/2003 | Assaker et al. ............ 606/61 |
| 6,669,700 B1 | 12/2003 | Farris et al. |
| 6,679,883 B2 * | 1/2004 | Hawkes et al. ............ 606/61 |
| 6,692,503 B2 * | 2/2004 | Foley et al. ................ 606/96 |
| 6,695,846 B2 | 2/2004 | Richelsoph et al. |
| 6,755,833 B1 | 6/2004 | Paul et al. |
| 6,761,719 B2 | 7/2004 | Justis et al. |
| 6,764,489 B2 * | 7/2004 | Ferree ........................ 606/61 |
| 2001/0014807 A1 | 8/2001 | Wagner et al. |
| 2001/0021851 A1 | 9/2001 | Eberlein et al. |
| 2001/0037112 A1 | 11/2001 | Brace et al. |
| 2001/0041894 A1 | 11/2001 | Campbell et al. |
| 2001/0047172 A1 | 11/2001 | Foley et al. |
| 2001/0047174 A1 | 11/2001 | Donno et al. |
| 2002/0013586 A1 | 1/2002 | Justis et al. |
| 2002/0022843 A1 | 2/2002 | Michelson |

| | | | | | |
|---|---|---|---|---|---|
| 2002/0045896 A1 | 4/2002 | Michelson | EP | 1 106 144 | 6/2001 |
| 2002/0045898 A1 | 4/2002 | Freid et al. | EP | 1 169 971 | 1/2002 |
| 2002/0045899 A1 | 4/2002 | Errico et al. | EP | 1 306 058 | 7/2002 |
| 2002/0049444 A1 | 4/2002 | Knox | EP | 1 285 632 | 2/2003 |
| 2002/0058939 A1 | 5/2002 | Wagner et al. | EP | 0 809 971 | 4/2003 |
| 2002/0065517 A1 | 5/2002 | Paul | EP | 1 336 383 | 8/2003 |
| 2002/0068938 A1 | 6/2002 | Jackson | EP | 1 346 697 | 9/2003 |
| 2002/0077630 A1 | 6/2002 | Lin | EP | 1 364 623 | 11/2003 |
| 2002/0111630 A1 | 8/2002 | Ralph et al. | FR | 1505513 | 12/1967 |
| 2002/0120268 A1 | 8/2002 | Berger | FR | 2435243 | 4/1980 |
| 2002/0120271 A1 | 8/2002 | Dixon et al. | FR | 2519857 | 7/1983 |
| 2002/0120272 A1 | 8/2002 | Yuan et al. | FR | 2556583 | 6/1985 |
| 2002/0120273 A1 | 8/2002 | Needham et al. | FR | 2740321 | 4/1997 |
| 2002/0128654 A1 | 9/2002 | Steger et al. | FR | 2778088 | 11/1999 |
| 2002/0128655 A1 | 9/2002 | Michelson | FR | 2810532 | 12/2001 |
| 2002/0151893 A1 | 10/2002 | Santilli | SU | 1424824 | 9/1988 |
| 2002/0151899 A1* | 10/2002 | Bailey et al. .................. 606/69 | WO | WO 88/03781 | 6/1988 |
| 2002/0173790 A1 | 11/2002 | Chang et al. | WO | WO 91/03994 | 4/1991 |
| 2002/0183754 A1 | 12/2002 | Michelson | WO | WO 95/25474 | 9/1995 |
| 2002/0183755 A1 | 12/2002 | Michelson | WO | WO 95/31941 | 11/1995 |
| 2002/0183756 A1 | 12/2002 | Michelson | WO | WO 96/05778 | 2/1996 |
| 2002/0183757 A1 | 12/2002 | Michelson | WO | WO 96/08206 | 3/1996 |
| 2002/0188296 A1 | 12/2002 | Michelson | WO | WO 97/22306 | 6/1997 |
| 2003/0018335 A1 | 1/2003 | Michelson | WO | WO 98/51226 | 11/1998 |
| 2003/0023242 A1 | 1/2003 | Harrington, Jr. | WO | WO 99/21502 | 5/1999 |
| 2003/0040749 A1 | 2/2003 | Grabowski et al. | WO | WO 00/24325 | 5/2000 |
| 2003/0045880 A1 | 3/2003 | Michelson | WO | WO 00/64359 | 11/2000 |
| 2003/0060828 A1 | 3/2003 | Michelson | WO | WO 00/66011 | 11/2000 |
| 2003/0078583 A1 | 4/2003 | Biedermann et al. | WO | WO 00/78238 | 12/2000 |
| 2003/0083658 A1 | 5/2003 | Hawkes et al. | WO | WO 01/01874 | 1/2001 |
| 2003/0093082 A1 | 5/2003 | Campbell et al. | WO | WO 01/26566 | 4/2001 |
| 2003/0105462 A1 | 6/2003 | Haider | WO | WO 01/26567 | 4/2001 |
| 2003/0130661 A1 | 7/2003 | Osman | WO | WO 01/49191 | 7/2001 |
| 2003/0149434 A1 | 8/2003 | Paul | WO | WO 01/89400 | 11/2001 |
| 2003/0153920 A1 | 8/2003 | Ralph et al. | WO | WO 01/89428 | 11/2001 |
| 2003/0181912 A1 | 9/2003 | Michelson | WO | WO 02/076317 | 10/2002 |
| 2003/0187440 A1 | 10/2003 | Richelsoph et al. | WO | WO 02/080789 | 10/2002 |
| 2003/0187441 A1 | 10/2003 | Bolger et al. | WO | WO 03/007826 | 1/2003 |
| 2003/0187442 A1 | 10/2003 | Richelsoph et al. | WO | WO 03/071966 | 9/2003 |
| 2003/0187509 A1 | 10/2003 | Lemole, Jr. | WO | WO 2004/071276 | 8/2004 |
| 2003/0191471 A1 | 10/2003 | Michelson | | | |
| 2003/0191472 A1 | 10/2003 | Michelson | | | |
| 2003/0208204 A1 | 11/2003 | Bailey et al. | | | |
| 2003/0225409 A1 | 12/2003 | Freid et al. | | | |
| 2004/0030338 A1 | 2/2004 | Paul | | | |
| 2004/0087951 A1 | 5/2004 | Khalili | | | |
| 2004/0092939 A1 | 5/2004 | Freid et al. | | | |
| 2004/0097934 A1 | 5/2004 | Farris et al. | | | |
| 2004/0097935 A1 | 5/2004 | Richelsoph et al. | | | |
| 2004/0097950 A1 | 5/2004 | Foley et al. | | | |
| 2004/0122426 A1 | 6/2004 | Michelson | | | |
| 2004/0127896 A1 | 7/2004 | Lombardo et al. | | | |
| 2004/0127899 A1 | 7/2004 | Konieczynski et al. | | | |
| 2004/0204710 A1 | 10/2004 | Patel et al. | | | |
| 2004/0220571 A1 | 11/2004 | Assaker et al. | | | |
| 2005/0038436 A1 | 2/2005 | Michelson | | | |
| 2005/0049593 A1 | 3/2005 | Duong et al. | | | |
| 2005/0192577 A1 | 9/2005 | Mosca et al. | | | |
| 2005/0283152 A1 | 12/2005 | Lindemann et al. | | | |

FOREIGN PATENT DOCUMENTS

| | | |
|---|---|---|
| DE | 28 08 971 | 9/1979 |
| DE | 44 09 833 | 10/1995 |
| EP | 0 201 024 | 11/1986 |
| EP | 0 410 309 | 1/1991 |
| EP | 0 455 255 | 11/1991 |
| EP | 0 599 640 | 6/1994 |
| EP | 0 809 972 | 12/1997 |
| EP | 0 897 697 | 2/1999 |
| EP | 0 903 113 | 3/1999 |
| EP | 0 988 833 | 3/2000 |
| EP | 0 995 404 | 4/2000 |

OTHER PUBLICATIONS

"CSLP Variable Angle: For Use with the Cervical Spine Locking Plate System," Technique Guide, 2000 SYNTHES® Spine, 14 sheets double-sided.

Zdeblick, M.D., Thomas A. et al. "Premier™ Anterior Cervical Plate System." Surgical Technique, 2000 Medtronic Sofamor Danek, 15 sheets double-sided.

Health Journal, Tara Parker-Pope, The Wall Street Journal, Jan. 2001, 1 sheet.

C-TEK Anterior Cervical Plate, 2001 Interpore Cross International, 1 sheet.

C-TEK Anterior Cervical Plate System, Interpore Cross, Oct. 2000, 1 sheet.

WINDOW Cervical Stabilization System, 2000 Endius, Inc., 10 sheets.

CASPAR Instruments for Anterior Cervical Fusion, AESCULAP, date unknown, 2 sheets double-sided.

NDC Internet data sheets, date unknown, 3 sheets.

Ni-Ti alloy Internet Data Sheets, printed Dec. 5, 2001, 2 sheets double-sided.

AESCULAP, Advanced Biomechanical Concept, date unknown, 11 sheets.

ORIA Zenith, Product Specifications, Mar. 2003, 18 sheets.

ZENITH, the perfect alliance for successful cervical fusions, Internet data sheets downloaded Apr. 2003, 2 sheets.

U.S. Appl. No. 10/014,409, filed Dec. 14, 2001, Bone Support Assembly, 7 sheets double-sided.

"The Market for Spinal Implants," Internet data sheets downloaded May 2001, 4 sheets.

* cited by examiner

SPINAL PLATE ASSEMBLY

CROSS-REFERENCE TO RELATED APPLICATIONS

This application claims priority under 35 U.S.C. §120 to application Ser. No. 10/202,705 filed Jul. 24, 2002, now U.S. Pat. No. 7,070,599, and to application Ser. No. 10/014,409 filed Dec. 14, 2001, now U.S. Pat. No. 6,755,833, all the above of which are incorporated herein by reference in their entireties.

BACKGROUND

The present invention relates to devices for the fixation and/or support of bones. In particular, the present invention relates to a spinal plate assembly, and a corresponding spinal plate, for the fixation and/or support of bones of the spinal column. The plate of the present invention has particular application in situations where compressional or settling forces, as well as torsional and flexing forces, of "fixed" vertebrae on a spinal plate cause significant stressing and potential failure of the spinal plate and/or plate components.

Vertebral fixation has become a common approach to treating spinal disorders and fractures, and for fusion of vertebrae at the time such fixation is instituted. Namely, one or more vertebrae are fixed in position relative to one or more other vertebrae above and/or below the vertebrae to be fixed. Generally, a spinal plate is the device of choice used for mechanically supporting such vertebral fixation. A typical spinal plate includes a plate having a plurality of apertures therethrough. A plurality of fasteners, i.e., bone screws, are generally positioned into and through respective ones of the apertures of the plate to thereby attach the spinal plate to bone, such as to two or more respective upper and lower supporting adjacent spinal vertebrae. The screws are fastened to the respective support vertebrae to thereby attach the spinal plate to the respective vertebrae. In general, such plate and screw assemblies can be utilized, for example, for anterior fixation of the spine for cervical, lumbar, and/or thoracic fixation.

The basis of anterior fixation or plating is to approach the spine from an anterior or anterio-lateral approach, and use the screws to solidly mount the spinal plate to the affected vertebrae. In addition to the application of a spinal plate, a graft material may be combined in an attempt to permanently fuse together adjacent vertebrae. The graft material can consist of bone grafts obtained from bones of the recipient or another individual.

A common problem associated with the use of such spinal plates is the tendency of the bone screws to "back out" or pull away or otherwise withdraw from the bone into which they are mounted. This problem occurs primarily due to the normal torsional and bending motions of the body and spine. This is a particularly important problem because as the screws become loose and pull away or withdraw from the bone, the heads of the screws can rise above the surface of the spinal plate and, possibly, even work their way completely out of the bone. While this condition can cause extreme discomfort for the recipient user of the spinal plate, this condition can also create a number of potentially serious physiological problems given the significant amount of nervous and vascular structures located at or near the potential locations of anterior spinal plate fixations.

A number of plate assembly designs have been proposed in attempts to prevent screws from pulling away or withdrawing from the bone and/or to prevent the screws from backing out or pulling away or withdrawing from the surface of the spinal plate. Such mechanisms used to prevent bone screws from pulling out of bones include cams which engage and lock the screws, and the use of expanding head screws which expand outwardly when adequate force is applied thereto to engage the holes in the spinal plate. All of these designs have detriments, which include potential for breakage of the screws, or which require particular precision and alignment in their application in order to work correctly. Additionally, loose components and accessories of spinal plates, which address the "backing-out" or withdrawal problem, can get dropped and/or misplaced while the vertebral fixation surgical procedure is taking place, prolonging and complicating the procedure as well as creating substantial risk of harm to the recipient.

Yet another common problem associated with the use of such spinal plates is the tendency, of the vertebrae which are being treated to settle after the spinal plate has been installed. Such settling adds compression forces to the above-listed forces, and raises the probability that the bone screws will break, will back out, or pull away, or otherwise withdraw, from the bone to which they were mounted.

It is an object of the invention to provide spinal plate assemblies which facilitate secure bone-to-bone fixation and/or support, such as at e.g. adjacent or second adjacent vertebrae, while accommodating post-procedural compression between the respective bones.

It is another object of the invention to provide spinal plate assemblies which afford substantial protection against pulling away or withdrawal of mounting components, which pulling away or withdrawal may result from e.g. torsional movement, flexing movement, or stress and/or dynamic load sharing of the vertebrae, the protection thereby enhancing the bone rebuilding process carried on routinely by the living body.

It is yet another object of the invention to provide spinal plate assemblies which attenuate application of stress on the plate apparatus and on the affixing components.

It is a further object of the invention to provide spinal plate assemblies comprising a spinal plate and resiliently movable spring-like material having resilient properties, the assemblies being so mounted and positioned as to enable bone fasteners to move past such spring-like material, with corresponding flexing or other movement of such spring-like material, when the bone fasteners are being installed in a recipient user and which, in combination with the designs of the bone fasteners, prevent unintentional withdrawal of the bone fasteners after installation of the bone fasteners in the recipient user.

It is yet a further object of the invention to provide spinal plate assemblies which can be completely pre-assembled such that no assembly steps need be performed on the spinal plate assembly, itself, while the spinal plate assembly is being installed in a recipient user thereof.

It is still a further object of the invention to provide spinal plate assemblies wherein apparatus, in such spinal plate assemblies, for preventing withdrawal of bone fasteners from the bone, after installation of the bone fasteners in a recipient user, are automatically activated, to prevent such withdrawal, as a consequence of the installation of suitably-configured such bone fasteners.

SUMMARY

This invention provides novel spinal plate assemblies, methods of fabricating such spinal plate assemblies, and methods of using such spinal plate assemblies. Such spinal plate assembly comprises a blocking structure assembled to a spinal plate. The blocking structure comprises first and second optionally elongate bands, biased against each other, or a single band biased against itself and a sidewall of the a channel in the plate. The bands are juxtaposed proximate, and extend into, fastener-receiving-apertures in the spinal plate. The bands are effective, automatically and as a consequence of driving of a bone fastener through the respective aperture, to respond to a side force applied by an interfering element of the bone fastener by resiliently moving transversely of the length of the longitudinal axis of the plate and away from the interfering element, and by resiliently returning to a blocking position over the interfering element after the interfering element passes the band.

In a first family of embodiments, the invention comprehends a spinal plate assembly. The spinal plate assembly comprises a spinal plate, the spinal plate comprising a top surface, a bottom surface opposite the top surface, which bottom surface is adapted to be positioned adjacent bone structure of a recipient user, and a plurality of bone-fastener-receiving apertures adapted to receive bone fasteners therethrough for mounting the spinal plate assembly to bone structure of the recipient user. The spinal plate further comprises a length and a width, and a thickness between the top surface and the bottom surface, channel structure extending alongside respective ones of the apertures and generally aligned with the top surface of the spinal plate, the channel structure comprising at least one channel having a collective length, a bottom, and first and second sides, at least one of the first and second sides of the at least one channel having an opening therein extending into a respective one of the fastener-receiving apertures. The assembly further comprises blocking structure in respective ones of the at least one channel, the blocking structure in a given channel having a length, and comprising first and second bands having respective lengths thereof, and extending along the length of the respective channel, and restoration structure having restorative spring-like properties and extending between, and connecting, the first and second bands, and urging the first and second bands into engagement with the first and second sides of the respective channel. At least one of the first and second bands extends through the opening in the respective side of the channel, and thus extends into the respective aperture, the band being effective, as a consequence of driving a bone fastener through the respective aperture, to respond to a side force applied by an interfering element of the bone fastener by moving transversely of the length of the respective the band, and away from the interfering element, and by returning to a blocking position over the interfering element after the interfering element passes the band, whereafter the position of the band over the interfering element is effective to inhibit withdrawal of the bone fastener, past the band, and out of the spinal plate assembly.

In some embodiments, the first and second bands comprise resiliently flexible bands, lengths of the bands extending alongside corresponding ones of the apertures whereby, as a bone fastener is driven, a control structure of the bone fastener urges the band to flex transversely of the length of the band, from a first flexural condition, until the control structure in the bone fastener is driven past the band, whereupon the band resiliently returns from the flexed condition and overlies the control structure of the so-driven bone fastener and thereby inhibits, typically prevents, the bone fastener from withdrawing the control structure past the band.

In some embodiments, the channel structure extends along the length of the spinal plate past at least a first row of the apertures and opens into each of the bone-fastener-receiving apertures in the respective row.

In some embodiments, all of the bone-fastener-receiving apertures comprise circular projected openings, and thus have substantially equal lengths and widths.

In other embodiments, at least all except two, and preferably all, of the bone-fastener-receiving apertures have greater projected lengths, along the length of the spinal plate, than projected widths transverse to the length of the spinal plate, and thereby comprise slots, all of the slots having commonly oriented axes along elongate dimensions of the slots, enabling longitudinal movement of bone fasteners in the slots, with respect to the spinal plate after the spinal plate assembly has been installed in a recipient user, thereby to accommodate settling of respective bones to which and adjacent which the spinal plate assembly is affixed.

In some embodiments, the spinal plate assembly comprises first and second rows of the bone-fastener-receiving apertures extending along the length of the spinal plate, the channel structure comprising a channel extending along the length of the spinal plate, sides of the channel opening into each aperture in the first and second rows of apertures, the first and second elongate bands being urged against the respective first and second sides of the channel, the first elongate band extending into and across portions of respective apertures in the first row, the second elongate band extending into and across portions of respective apertures in the second row.

In preferred embodiments, the retaining structure comprises the first and second bands and the restoration structure, the restoration structure comprising one or more compression springs extending between, and directly or indirectly interfacing with, the first and second bands.

Preferably, the first and second bands, in combination with the compression springs, define a unitary structure derived from a single unitary work piece.

In some embodiments, the first and second bands extend along substantially full lengths of respective first and second sides of the channel, and the first and second bands collectively extend into and across portions of each of the bone-fastener-receiving apertures.

In preferred embodiments, the assembly comprises first and second rows of the bone-fastener-receiving apertures extending along the length of the spinal plate, the at least one channel comprising a channel extending along the length of the spinal plate, and first and second overhanging top retaining walls of the channel extending inwardly from the sides of the channel and spaced from each other, thereby leaving an opening in the top of the channel between the overhanging top retaining walls and extending along the length of the channel, the overhanging top retaining walls being effective as retainers to restrain movement of the blocking structure out of the channel through the top of the channel.

In some embodiments, the assembly comprises first and second band retainers extending from at least one of the first and second bands, each band retainer on a respective the band extending inwardly toward the other band, and at least one stud extending into the channel and interacting with the band retainers and the plate so as to prevent substantial longitudinal movement of the blocking structure along the length of the channel.

In some embodiments the first and second elongate bands are urged, by the at least one restorative structure, against the respective first and second sides of the channel, and thus into and across a portion of each respective aperture in the first and second rows.

In some embodiments, the first and second band retainers are substantially spaced longitudinally from each other along the length of the blocking structure, and interact with first and second respective studs, spaced from each other, the studs being disposed adjacent respective ones of the retainers so as to prevent substantial movement of the blocking structure along the length of the channel.

In other embodiments, the first and second band retainers are closely spaced longitudinally with respect to each other, and interact with a common stud, on opposing sides of the stud, so as to prevent substantial movement of the blocking structure along the length of the channel.

In some embodiments, the first and second bands extend alongside corresponding ones of the apertures whereby, as a bone fastener is driven, a control structure of the bone fastener urges the respective band to move from a first position transversely of the length of the band, with corresponding flexing of the at least one restorative structure, from a first flexural condition, until the control structure in the bone fastener is driven past the band, whereupon the restorative structure returns the band to substantially the first position, whereupon the band overlies and blocks the control structure of the so-driven bone fastener and thereby prevents the bone fastener from withdrawing the control structure past the band.

In some embodiments, the at least one restorative structure comprises at least two springs extending as compressible folded leaves between the first and second bands.

In preferred embodiments, the first and second bands, and the at least one restorative structure, define a unitary structure derived from a single unitary work piece.

In some embodiments, the compositions of the bands are selected from the group consisting of titanium, titanium alloy, and stainless steel.

In other embodiments, the retaining structure comprises a plastic composition which is safe for use in living human or animal bodies, as an implantable plastic, and which retaining structure has suitable strength, rigidity, and deflection properties to perform the desired functions in an anticipated implant use environment.

In preferred embodiments, such plastic composition of the retaining structure comprises one or more materials selected from the group consisting of polyetherimide copolymer, acetal copolymer, polyethersulfone, polyarylethersulfone, polycarbonate, ultra high molecular weight polyethylene, polyetheretherketone, and polyaryletherketone, and blends and mixtures of the materials.

In preferred embodiments, the bands are sufficiently small in cross-section, and are properly positioned over the apertures, so as to let the bone fastener pass below a respective band, with transverse movement of the band, and without exceeding a flexural limit of the at least one restorative structure, such that the restorative structure then returns the band to a blocking position over the bone fastener.

In preferred embodiments, the at least one restorative structure comprises a substantially straight line compression spring, preferably at least three substantially straight line compression springs, integral with the first and second bands, and wherein the spring, in combination with the first and second bands, defines a unitary structure derived from a unitary work piece.

In some embodiments, the channel structure is expressed intermittently along the length of the plate.

In some embodiments, the bone-fastener-receiving apertures are spaced along the length of the spinal plate, the channel structure comprises an elongate channel extending along the length of the spinal plate, the blocking structure comprises a plurality of band structures positioned in the channel, disposed lengthwise of each other, and disposed alongside respective ones of the apertures, and spacers are positioned between respective adjacent band structures so as to inhibit substantial longitudinal movement of the band structures.

In some embodiments, the spacers are held in position in the channel by studs extending through the spinal plate and into the channel, and into cooperating apertures in the respective spacers.

The invention is also expressed in a family of embodiments which comprehend a method of fabricating a spinal plate assembly. The method comprises providing a spinal plate having a top surface, a bottom surface opposite the top surface, the bottom surface being adapted to be positioned adjacent bone structure of a recipient user, and a plurality of bone-fastener-receiving apertures are adapted to receive bone fasteners therethrough for mounting the spinal plate assembly to the bone structure of the recipient user, the spinal plate further comprising a length and a width, and a thickness between the top surface and the bottom surface, and channel structure extending along the length of the spinal plate, the channel structure having a collective length, a bottom, a top, and first and second sides, at least one of the first and second sides of the channel having an opening therein extending into a respective one of the bone-fastener-receiving apertures, the channel having an opening on at least one end of the spinal plate; inserting longitudinally into the channel, through the opening at the end of the spinal plate, a blocking structure, the blocking structure having a length and comprising first and second bands connected to each other by a plurality of spaced resiliently compressible restorative structures; and locking the blocking structure in the channel.

In some embodiments, the spinal plate defines first and second overhanging top walls of the channel, extending inwardly from the sides of the channel, the overhanging top walls being effective as band retainers to restrain movement of the blocking structure out of the channel through the top of the channel.

In a third family of embodiments, the invention comprehends a method of installing a spinal plate assembly in a recipient user thereof. The method comprises providing, at the installation site in the recipient user, a spinal plate assembly comprising (i) a spinal plate having a top surface, a bottom surface opposite the top surface, the bottom surface being adapted to be positioned adjacent bone structure of a recipient user, and a plurality of bone-fastener-receiving apertures adapted to receive bone fasteners therethrough for mounting the spinal plate assembly to the bone structure of the recipient user, the spinal plate further comprising a length and a width, and a thickness between the top surface and the bottom surface, and channel structure extending along the length of the spinal plate, the channel structure having a collective length, a bottom, a top, and first and second sides, at least one of the first and second sides of the channel having an opening therein extending into a respective one of the bone-fastener-receiving apertures, the channel having an opening on at least one end of the spinal plate, and (ii) blocking structure in the channel, the blocking structure having a length and comprising first and second bands connected to each other by a plurality of spaced resiliently compressible springs, biasing the first and second bands against each other and urging the first and second bands into engagement with the first and second sides of the channel when the blocking structure is in the channel, whereby the first and second bands extend into, and across, portions of the bone-fastener-receiving apertures; and advancing bone fasteners through selected ones of the bone-fastener-receiving apertures and into bone structure of the recipient user, including advancing interfering control structure of the bone fasteners past respective elements of one or more of the first and second bands, such that a given interfering control structure of a respective fastener causes the respective band to deflect from a first position, transversely of the length of the band as the interfering control structure passes and such that, when the interfering control structure moves past the band, the band returns to the first position, thereby occupying a blocking position, whereby the blocking structure is effective to automatically inhibit withdrawal of the bone fastener, past the band.

In a fourth family of embodiments, the invention comprehends a spinal plate assembly. The spinal plate assembly comprises a spinal plate, the spinal plate comprising a top surface, a bottom surface opposite the top surface, the bottom surface being adapted to be positioned adjacent bone structure of a recipient user, and a plurality of bone-fastener-receiving apertures adapted to receive bone fasteners therethrough for mounting the spinal plate assembly to the bone structure of the recipient user, the spinal plate further comprising a length and a width, and a thickness between the top surface and the bottom surface, channel structure extending alongside respective ones of the apertures and generally aligned with the top surface of the spinal plate, the channel structure comprising at least one channel having a collective length, a bottom, and first and second sides, at least one of the first and second sides of the at least one channel having an opening therein extending into a respective bone-fastener-receiving aperture; and blocking structure in respective ones of the at least one channel, the blocking structure in a given channel having a length, and comprising at least a first band having a length, and extending along a side of the channel, the at least one band being resiliently urged into engagement with the side of the channel. The band extends across the opening in the respective side of the channel, and thus extends into the respective aperture, the band being effective, as a consequence of driving a bone fastener through the respective aperture, to respond to a side force applied by an interfering element of the bone fastener by moving transversely of the length of the respective band, and away from the interfering element, and by returning to a blocking position over the interfering element after the interfering element passes the band, whereafter the position of the band over the interfering element is effective to inhibit withdrawal of the bone fastener, past the band, and out of the spinal plate assembly.

Figure 1:
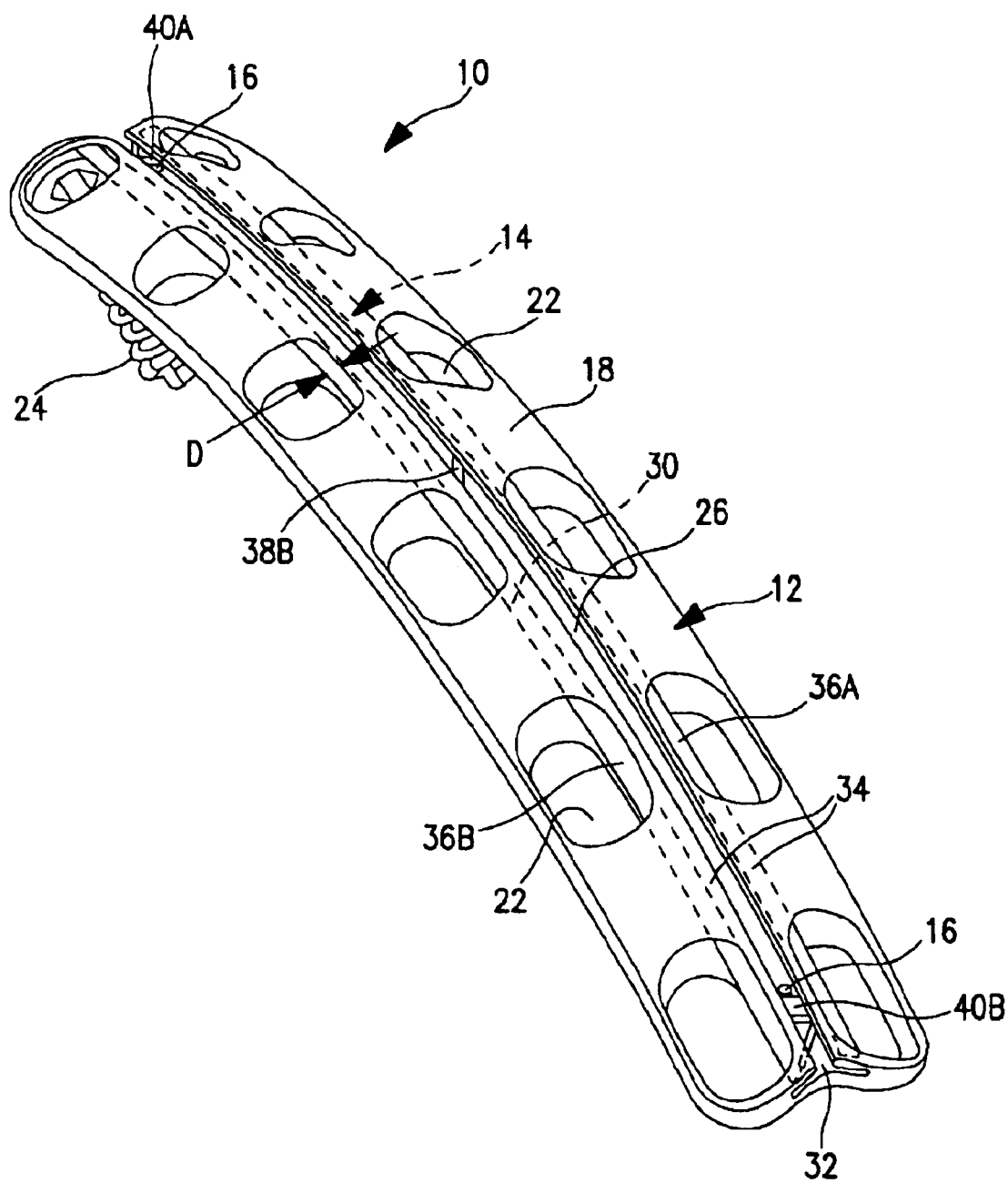
FIG. 1 shows a pictorial view of a first embodiment of spinal plate assemblies of the invention, including a spinal plate.

The invention is not limited in its application to the details of construction or the arrangement of the components set forth in the following description or illustrated in the drawings. The invention is capable of other embodiments or of being practiced or carried out in other various ways. Also, it is to be understood that the terminology and phraseology employed herein is for purpose of description and illustration and should not be regarded as limiting. Like reference numerals are used to indicate like components.

DESCRIPTION OF THE ILLUSTRATED EMBODIMENTS

Referring now to the embodiments represented by FIGS. 1–5, a spinal plate assembly 10 of the invention includes a spinal plate 12, a blocking structure generally represented by 14 in FIG. 1, and one or more retaining structures 16.

Spinal plate 12 has a top surface 18, a bottom surface 20 adapted to be positioned adjacent bone structure of a recipient user of the spinal plate assembly, and a plurality of bone-fastener-receiving apertures 22 which receive bone fasteners such as bone screws 24. Apertures 22 are arranged in first and second rows of such apertures, along the length of the spinal plate.

Top surface 18 of the spinal plate defines a channel 26 extending along the length of the spinal plate. Channel 26 has a bottom wall 28, opposing side walls 30, and has openings 32 extending out the respective ends of spinal plate 12, best illustrated in FIG. 5. An opening 32 is also illustrated in FIG. 1. Channel 26 further has overhanging top walls 34 extending inwardly from the side walls of the channel and spaced from each other, thereby leaving an opening 35 in the top of the channel between the overhanging top walls and extending along the length of the channel. Opening 35 can be eliminated if desired. The dimension of the open cross-section of the channel, as defined between side walls 30 and top and bottom walls 28 and 34, is preferably generally consistent along substantially the full length of the support plate. Side walls 30 of the channel are specifically located and configured so as to open into the sides of, and extend along and inwardly of the sides of, apertures 22. In general, imaginary extensions of side walls 30 project across apertures 22 at locations displaced inwardly of the aperture side walls by distance "D" of about 1 mm.

Figure 6A:
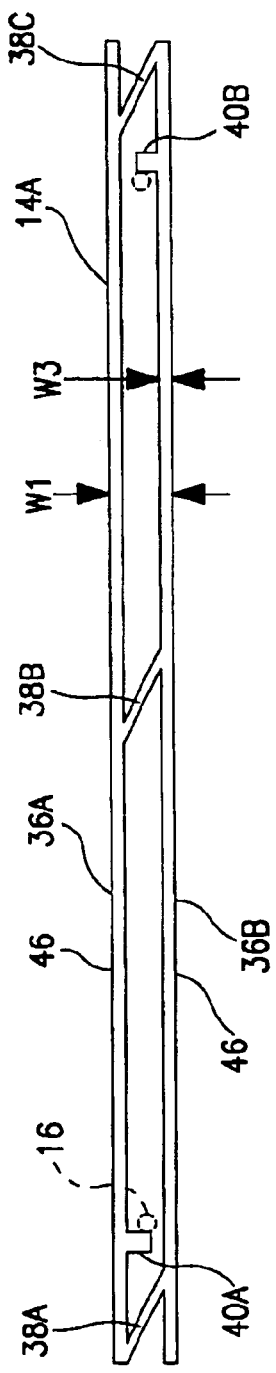
FIG. 6A shows a top view of a first embodiment of blocking structures which are incorporated into spinal plate assemblies of the invention, and wherein the longitudinal retainers are substantially spaced from each other, and extend from opposing bands.

FIG. 6A illustrates the blocking structure 14A which is incorporated into the assembly illustrated in FIG. 1. As seen in FIG. 6A, blocking structure 14A includes first and second elongate bands 36A, 36B extending parallel to each other and in a common plane. Bands 36A, 36B are connected to each other by three substantially straight line compression springs 38A, 38B, 38C mounted to bands 36A, 36B at straight line angles of about 10 degrees to about 30 degrees to the respective bands. First and second band retainers 40A, 40B extend from the respective bands 36A, 36B, toward the opposing bands. Thus, retainer 40A is disposed proximate the left end of band 36A and extends toward band 36B. Correspondingly, retainer 40B is disposed proximate the right end of band 36B and extends toward band 36A.

Leaf springs 38A, 38B, 38C represent only one of a wide variety of options regarding compression spring loading of the bands for biasing the bands against each other and thus for displacement of the bands away from each other. While 3 springs are shown, any number of springs can be used, with suitable adjustment of the force exerted by each spring.

Referring to FIGS. 1 and 6A, retaining structure 16 comprises first and second retainer studs which extend, by friction fitment, through apertures 44 in the bottom wall of support plate 12, and thence into channel 26 and into abutment with band retainers 40A, 40B. Studs 16 are shown in solid outline in FIG. 1, and are shown, to illustrate their relative locations, in dashed outline in FIG. 6A.

The width "W1" of blocking structure 14 between the outer walls 46 of bands 36A, 36B is slightly greater at rest than the width "W2" of channel 26 between side walls 30. Blocking structure 14 is inserted longitudinally into channel 26 by squeezing the blocking structure together at the width dimension thereof, at least at an end of the blocking structure, sufficient to temporarily reduce the width "W1" of the blocking structure to a width less than width "W2" of channel 26; and by at the end of channel 26. As the blocking structure is squeezed, the squeezing is progressively resisted by the resilience of the compression springs 38A, 38B, 38C between the bands. The spring closest to the end being squeezed together is most affected in resisting such squeezing, thereby setting up a resilient force urging restitution of the compressive squeezing force, and thus urging the outer walls 46 of the blocking structure into engagement with side walls 30 of the channel as the blocking structure is being inserted longitudinally into channel 26. As the insertion of the blocking structure progresses into channel 26, the respective compression springs 38 become progressively squeezed as they enter channel 26, each developing a resilient outwardly-directed force urging the outer walls 46 of the bands into engagement with side walls 30 of the channel.

Since the side walls of the channel open into apertures 22, bands 36A, 36B extend across apertures 22 as the blocking structure is inserted into channel 26. The length of blocking structure 14 as illustrated corresponds substantially with the length of channel 26 such that the entirety of the length of the blocking structure is received within channel 26, and wherein the blocking structure extends substantially the full length of channel 26. Where a single blocking structure is used, the length of the blocking structure should be at least great enough that bands 36A, 36B extend across each of the apertures 22 in the respective row of apertures.

Figure 10:
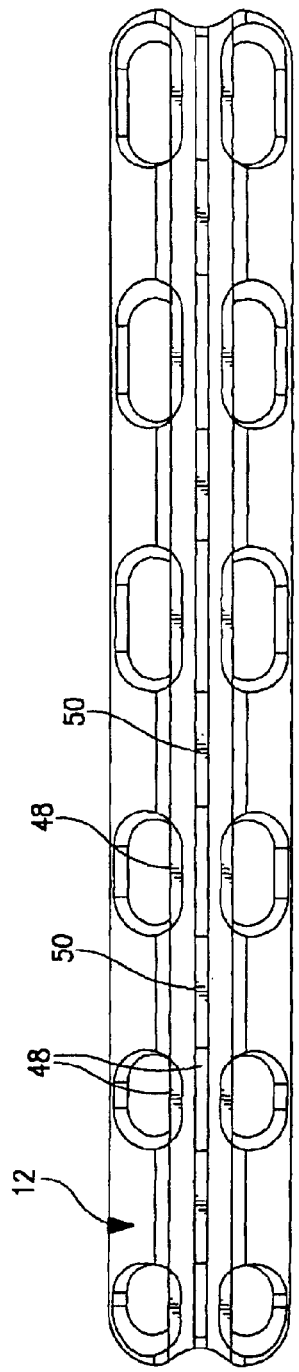
FIG. 10 is a top view of a spinal plate assembly of the invention employing a segmented blocking structure and all slot-shaped apertures.
Figure 11:
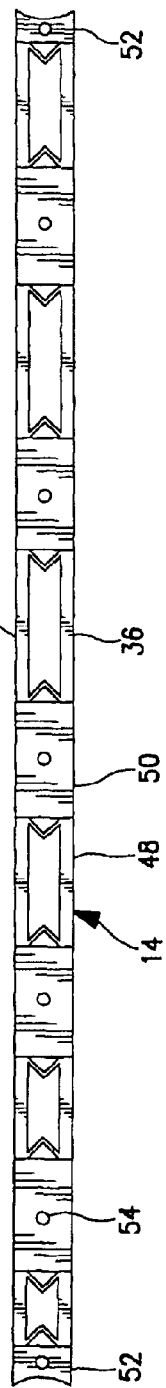
FIG. 11 shows a bottom view of the segmented blocking structure of FIG. 10, separated from the spinal plate.

In the alternative, channel 26 can be expressed intermittently. As illustrated in FIGS. 10 and 11, intermittent expression of the channel can be effected by placing spacers 50 in the channel at spaced locations. In an embodiment not shown, channel 26, itself, is intermittent, whereby the space shown occupied by spacers 50 in FIGS. 10, 11 is occupied, in the plate assembly, by material forming part of the structure of plate 12. Thus, channel 26 in such embodiments is expressed as a series of longitudinally spaced, and relatively shorter channels. Length of a given channel is sufficient to hold a band which extends into a respective adjacent aperture 22.

Once the blocking structure is thus installed in channel 26, retaining studs 16 are inserted through apertures 44 into channel 26. Studs 16 are sized to friction fit into apertures 44, and can be welded to plate 12 e.g. at the bottom surface of plate 12 if desired. Studs 16 extend into channel 26 a distance sufficient to come into close proximity with, optionally to come into abutting engagement with, band retainers 40A, 40B. In the embodiment illustrated in FIGS. 1 and 6A, the studs are between the two band retainers 40A, 40B, whereby the respective studs effectively interact with the band retainers so as to prevent substantial longitudinal movement of the blocking structure along the length of the channel. Thus, with the studs installed, the blocking structure is restrained from moving longitudinally along the length of the channel. At the same time, the bands 36A, 36B are being urged against the side walls of the channel by springs 38.

In the alternative, other retaining structure can be used to retain the bands and other elements of the blocking structure.

Blocking structure 14, including bands 36A, 36B, is thus effectively confined in channel 26. The blocking structure is effectively prevented from moving longitudinally by studs 16 or other retaining structure. The blocking structure is effectively prevented from moving laterally by side walls 30 of the channel. The blocking structure is effectively prevented from moving vertically by bottom wall 28 and overhanging top walls 34. Thus, once the blocking structure is inserted into the channel, and the studs 16 or other retaining structure are installed in interfering relationship with retainers 40A, 40B, the blocking structure is effectively locked into position in channel 26. In such position, bands 36A, 36B extend across portions of the respective apertures 22 as illustrated in e.g. FIGS. 1–3.

As shown in the various drawings, springs 38 extend between the respective bands 36A, 36B, and thus bias the bands with respect to each other. Thus, e.g. when squeezing force is applied to the blocking structure to reduce the overall width of the blocking structure thereby to enable the blocking structure to be inserted into channel 26, springs 38 are effectively biasing the bands against each other, such that a force exerted against a first one of the bands, and directed toward the other of the bands, is transferred at least in part to the other band, whereby the physical properties of the bands interact with each other when such force is applied.

Thus, springs 38 position bands 36 solidly against the side walls of the channel where the bands are not passing through apertures 22. With the bands solidly against the side walls of the channel, the outwardly-disposed walls 46 of the bands are in surface to surface contact with side walls 30 of the channel. The outwardly-disposed walls 46 of the bands, the spring-loading of the bands, the respective rows of apertures 22, overhanging top walls 34, and springs 38 are thus all correspondingly sized, arranged and configured with respect to each other such that bands 36 are trapped between the side walls, the channel bottom, the overhanging top walls, and the springs such that the bands, without external forces applied, extend along a path wherein outwardly-disposed walls 46 of the bands extend along side walls 30 of the channel. Since imaginary extensions of the side walls of the channel are displaced inwardly, into the apertures, of the aperture side walls by about 1 mm, the outwardly-disposed side walls of the bands also are displaced inwardly of the aperture side walls by a distance "D" of about 1 mm, and thus extend across corresponding portions of the projected cross-sections of the respective apertures.

Figure 6B:
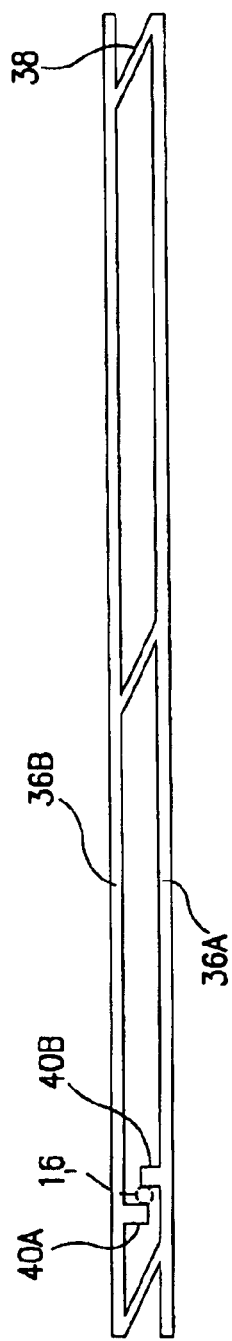
FIG. 6B shows a top view of a second embodiment of blocking structures which are incorporated into spinal plate assemblies of the invention, and wherein the longitudinal retainers are closely spaced from each other, and extend from opposing bands.

FIG. 6B illustrates a second embodiment of the blocking structure wherein the band retainers are spaced closely adjacent each other, with a single retaining stud 16, shown in dashed outline, interposed between the band retainers. The spacing between the band retainers is only great enough to enable stud 16 to be inserted between the retainers. Thus, the stud or other retainer is either in frictional engagement with both retainers, or is so close to both retainers that no more than negligible longitudinal movement can be effected by blocking structure 14 after the blocking structure is installed in channel 26, and stud 16 is installed between the retainers.

Whether the retainers are closely spaced as in FIG. 6B or are substantially spaced from each other, e.g. proximate ends of the blocking structure as in FIG. 6A, either retainer 40A, 40B can extend from either of the bands 36A, 368. FIGS. 6A and 6B show one such retainer from each such band 36A, 36B. In the alternative, both retainers can extend from the same band, either band 36A or band 36B.

Similarly, the position or positions of the stud or studs, with respect to the bands is not critical so long as the overall effect is that interaction of the bands with the stud or studs prevents the blocking structure from moving in either longitudinal direction in the channel. For example, FIG. 6A shows the studs both being disposed longitudinally inwardly of the retainers. The studs can as well both be disposed longitudinally outwardly of the retainers.

Springs 38 can employ a variety of spring structures and still perform effectively. Thus, FIGS. 6A and 6B show substantially straight line angle compression springs which typically define angles of about 10 degrees to about 30 degrees with the respective bands. Angles of about 15 degrees to about 20 degrees are preferred. Such springs are also known as "N" springs wherein the legs of the "N" are represented by bands 36A and 36B, and wherein the angled "N" connector extends between the two bands and provides the primary resilient restorative spring-like force.

The magnitude of the angle, in combination with the magnitude of the cross-section, in combination with the composition, of a spring 38 at least in part determines the spring constant, whereby any of the respective determinant parameters can be modified according to conventional knowledge in obtaining the desired spring constant, wherever advantage is to be obtained.

Springs 38 need not be straight line constructs. Rather, such springs can embody, for example and without limitation, a number of curvilinear shapes and angular shapes. Indeed a folded leaf construct is shown in FIGS. 10 and 11, as discussed further hereinafter. All that is required is that the spring provide the desired restitution force and distance of movement to bands 36A, 36B to accommodate installation of blocking structure 14 into channel 26, and passage of fasteners 24 accompanied by resilient restoration of the bands over the heads of the fasteners, whereby a wide range of spring structures are suitable for use as springs 38.

Figure 6C:
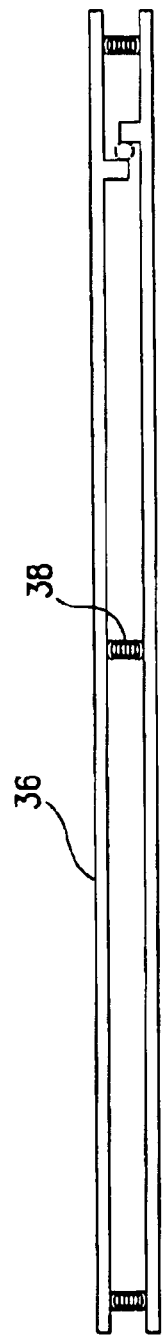
FIG. 6C shows a top view of a third embodiment of blocking structures which are incorporated into spinal plate assemblies of the invention, wherein the longitudinal retainers are closely spaced from each other and extend from opposing bands, and wherein the spring feature is represented by coiled compression springs.

As an exemplary alternative, FIG. 6C shows coil springs. As other alternatives, one can thus select from a wide range of conventionally available springs for use as springs 38.

Figure 7:
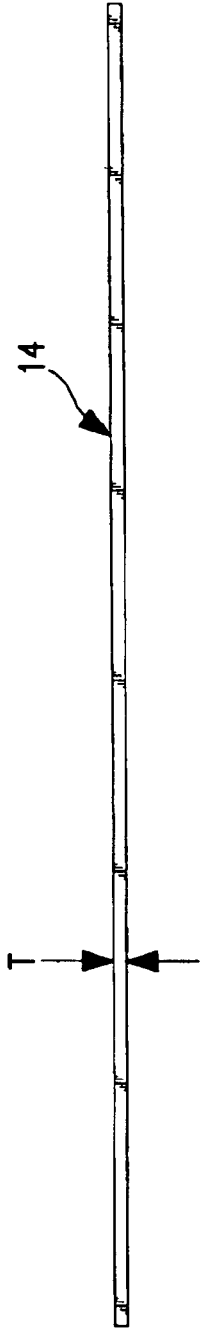
FIG. 7 shows a side elevation of the blocking structure of FIG. 6A.

FIG. 7 shows a side view of the blocking structure, illustrating the preferred uniform thickness "T" of the blocking structure along the length of the blocking structure.

Figure 8:
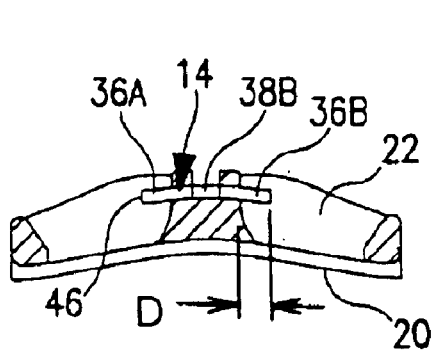
FIG. 8 shows a cross-section of the spinal plate assembly of FIGS. 1–4 and is taken at 8—8 of FIG. 4.
Figure 5:
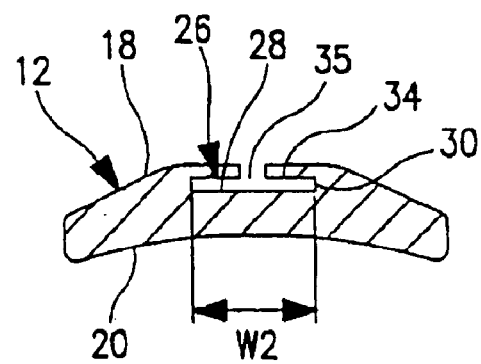
FIG. 5 shows a cross-section of the spinal plate illustrated in FIGS. 1–4, and is taken at 5—5 of FIG. 4.

FIG. 8 shows a cross-section of the spinal plate assembly of FIGS. 1–4 at an aperture 22. Thus, FIG. 8 shows bands 36A, 36B extending into apertures 22, as well as showing spring 38B biasing the bands into such position.

Figure 9A:
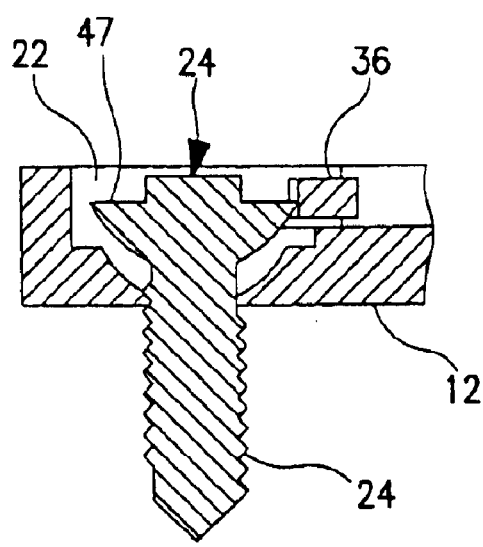
FIG. 9A is a cross-section of a spinal plate assembly as in FIGS. 1–4, showing the band deflected by the passing of the control structure, on the head of a bone screw in contact with the band.
Figure 9B:
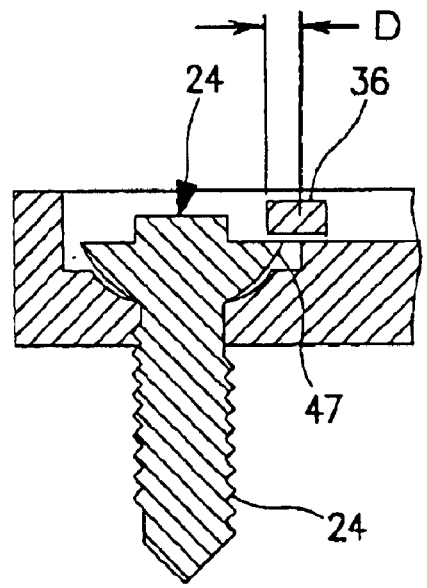
FIG. 9B is a cross-section as in FIG. 9A wherein the head of the bone screw has passed the bottom of the band thus to enable the band to revert to its undeflected and blocking position over the head of the bone screw.

FIGS. 9A and 9B illustrate the process by which a band 36 is flexed or deflected, or otherwise caused to move, when a bone screw 24 passes the band, and further illustrate the interference in a withdrawal path of the screw, provided by the band after the screw has been driven past the band and the band has returned to the undeflected condition.

Referring to FIG. 9A, as a bone screw is advanced through an aperture 22, the spring biasing of the band is effective, automatically and as a consequence of driving the bone screw through the respective aperture and into bone structure of a recipient user, to respond to side force applied by an interfering element 47 such as the outer portion of the head of the bone screw by resiliently moving transversely of the length of the band, and away from such interfering element, and by resiliently returning to a position over the interfering element after the interfering element passes the band. After returning over the interfering element, the position of the band over the interfering element is effective to inhibit withdrawal of the bone screw past the band and out of the spinal plate assembly.

Looking specifically at FIG. 9A, as the bottom surface (e.g. interfering element) of the outer portions of the head of the bone screw engages the top outer corner of the band, the beveled or conical bottom surface of the screw head urges the band out of interfering alignment under the screw head. Once the screw head, as an interfering element of the screw, has moved past the band, the band automatically returns to an interfering, blocking position over the outer edge of the screw head as shown in FIG. 9B. Such interfering, blocking position over the screw head is effective to interfere with, typically to block, withdrawal of that screw past that band. Thus, the band serves as a safety device preventing withdrawal of the bone screw from the bone, and from the spinal plate assembly.

FIGS. 10 and 11 illustrate a further family of embodiments of spinal plate assemblies of the invention. In the embodiments of FIGS. 10 and 11, plate 12 is substantially as shown and described in the previous embodiments. As noted hereinabove, blocking structure 14 is shown as a plurality of shortened band-spring combinations 48, with spacers 50 disposed between the respective band-spring combinations, and with end closures 52 at respective outer ends of the outer-most ones of the band-spring combinations. Thus, blocking structure 14 is expressed as intermittent placement of the band-spring combinations along the length of the plate, whereby channel 26 is effectively intermittent, with spacers 50 acting as barriers between the intermittent expressions of the channel.

In a family of embodiments (not shown), channel 26 can be intermittent, namely expressed intermittently, and exist only e.g. adjacent apertures 22. In such embodiments, bands 36A, 36B are held in channel elements which extend e.g. downwardly from top surface 18 of plate 12, and which channel elements thus define the band paths. Separate retaining structures 16 are not needed because end walls of the intermittent expressions of the channels prevent longitudinal movement of the bands, whereby the functions of the retainers are typically provided by material of the plate.

In still another family of embodiments, channel 26 can be constructed with blind ends, namely closed ends, whereby no end closures 52, and no studs 16, need be employed, as the channel end walls effectively prevent longitudinal movement of the bands.

Stud apertures 54 are shown in the bottom surfaces of spacers 50 and closures 52. Corresponding stud apertures 44 are also employed in plate 12 extending from the bottom surface of plate 12 to the bottom of channel 26. Studs are inserted through apertures 44 and into corresponding apertures 54, thus to fix the longitudinal positioning of the spacers and end closures. Where desired, less than all, in fact, none, of the spacers need employ such studs, since the spacers and band-spring combinations are effectively held in the channel by the studs employed at end closures 52.

FIGS. 10 and 11 illustrate a plurality of band-spring combination structures positioned in the channel, which can also be considered as intermittent expressions of a channel between spacers 50, and disposed alongside the respective pairs of apertures, with spacers 50 positioned between respective adjacent band structures so as to inhibit substantial longitudinal movement of the band structures, and to provide continuous end surfaces, at the ends of the spacers, against which the springs can flex inwardly as a bone screw is driven past the respective band. As shown, each band-spring combination includes a pair of bands 36 on opposing sides of the combination element, and first and second 2-direction leaf springs 38 at opposing ends of the combination element.

The spacers are held in position in the channel by studs extending through the spinal plate and into the channel, and into cooperating apertures in the respective spacers.

FIGS. 10 and 11 show a separate band-spring combination 48 for deployment adjacent each pair of apertures 22. As desired, fewer such band-spring combinations can be used wherein at least one such band-spring combination can extend across two or more such pairs of apertures.

Since spinal plate assemblies of the invention are to be used within living bodies, all materials used in the spinal plate assemblies must be compatible with, and safe for use inside, the living body. In that regard, preferred material for spinal plate 12, blocking structure 14, springs 38, and studs 16, is titanium, or titanium alloy, for example titanium-aluminum alloy. A specific titanium aluminum alloy referred to in ASTM F-136 is (Ti 6AL-4V). Other titanium alloys are contemplated. Preferred materials for bands 36 have a desired level of resilient flexural capacity. Safety is typically controlled by composition and structure. In this analysis, exemplary structure is shown in the drawings herein; and composition is the variable being analyzed.

Plate 12 has a length sufficiently long to span at least two vertebrae, and width and thickness sufficiently great to provide resistance to bending and torsion forces. Accordingly, where plate 12 is composed of one of the above referred-to materials, typical dimensions are as follows. Typical length is at least 20 mm, up to as great as about 120 or more mm. Width is typically about 15 mm to about 20 mm. Nominal thickness is typically about 2 mm to about 3.5 mm. The bottom of channel 26 is typically about 0.7 mm to about 1.5 mm from the top surface of the plate. Typical nominal depth of channel 26, from the bottom of the channel to any overhanging top wall, is about 0.5 mm. Such dimensions are, of course, exemplary only and not limiting and, given the above exemplary dimensions, those skilled in the art can vary such dimensions according to specific structure of respective plates and plate assemblies.

In addition, such materials must perform the required physical functions of flexing enough, when properly positioned over apertures 22, to let the bone screws pass below the bands without exceeding the flexural limits of the band materials or the springs, and must return to blocking positions over the screws or other control structure after passage of the bone screws. Such flexural properties are based on physical properties inherent in the material compositions, in combination with the physical cross-sections of the bands and springs.

The resilient properties can be provided by bands 36, by springs 38, or by a combination of bands 36 and springs 38. Thus, bands 36 can be substantially non-flexible and substantially all the resilience can be provided by the flexibility of springs 38. In the alternative the structures shown as springs 38 can be substantially non-flexible, namely can perform a rigid blocking function once installed in channel 26, whereby substantially all the resilience is provided by bands 36. Typically, the ability of bands 36 to move, in response to advance of a bone screw, is provided in part by each the band and at least one spring.

In preferred embodiments, bands 36 and springs 38 are fabricated from a single piece of material whereby the inherent physical properties of the bands and the springs are the same. Typically, the resilience in such combination is provided by the combination of springs 38 and bands 36. The resiliences provided by the respective bands and springs in such combination are nevertheless dependent on the respective widths and thicknesses of the bands and springs, as well as on the angles expressed between the spring leaves and the bands at any given time. Thus, the springs and bands can be engineered for a wide range of desired degrees of resilient restoration force to be provided by the respective bands and springs.

Accordingly, certain materials which are not generally considered as having resilient, spring-like properties can, when fabricated into sufficiently small cross-sections, perform the desired resiliently flexural spring function of the springs or the bands. For example and without limitation, bands 36 can employ titanium compositions, titanium alloy compositions such as titanium-aluminum alloy compositions such as the above-mentioned specific alloy, or other titanium alloys, or stainless steel compositions which, in sufficiently small cross-section, can exhibit the desired resilient spring-like properties. Other materials can be used as bands 36 and springs 38 so long as such materials satisfy the above safety and performance requirements.

Any of the plastic materials known to be safe for use in living human or animal bodies, as applies, as implantable plastics, and which have suitable hardness and rigidity, can be employed for fabricating bands 36. As with the metals, such materials must be both bio-stable and bio-compatible.

As such plastics, there can be mentioned, for example and without limitation, polyetherimide copolymer such as ULTEM®,
acetal copolymer,
polyethersulfone, also known as polyarylsulfone, such as RADEL A®, polyarylethersulfone such as RADEL R®,
polycarbonate,
ultra high molecular weight polyethylene,
polyetheretherketone, also known as PEEK, available from Boedecker Plastics, Inc. Shiner, Tex.,
polyaryletherketone, also known as PEEK-OPTIMA®.

Such materials can be filled or unfilled, and can employ the usual additives, including processing aids, so long as the resultant composition is suitable as an implantable plastic for use in a living, e.g. human, body.

As a result of the structures of apertures 22, channel side walls 30, and blocking structure 14, along with proper positioning of stud 16 or other retaining structure, when a bone screw, which properly fits the apertures 22, is driven through an aperture 22, the head of the bone screw impacts the respective band 36 as shown in FIG. 9A, and forces the band in a width-wise transverse direction away from the center of the aperture in order that the head of the bone screw can pass the band. Since the band is readily and resiliently moved, against resistance of springs 38, and since the bone screw is already embedded in bone material of the recipient user by the time the screw head reaches the band, the band moves in response to the urging of the head of the bone screw, as shown in FIG. 9A. When the head of the bone screw passes below the bottom of the band, the band is no longer being held in the moved position, and therefore resiliently returns to the position occupied prior to being moved, thereby setting up a potential interference between the band and the screw, of more or less about 1 mm, which interference is activated if and when the screw begins to back out of, or withdraw from, the spinal plate.

The invention contemplates that bands 36 can be arranged in other than a rest, or straight, condition when not being forced sideways by heads of bone screws. Thus, the bands can be under a degree of constant stress, e.g. pre-stressed condition, wherein the level of stress changes as the head of the screw passes, and then reverts to the previous level of stress after the screw head passes.

Similarly, bands 36 can be in a non-straight, e.g. curvilinear or angled, configuration when not being moved by a screw head or other interfering element, and can still move with respect to the bone screw as the bone screw is driven past the band.

Likewise, channel 26 can be intermittent, and can exist only adjacent apertures 22. FIG. 11 illustrates an effectively intermittent use of blocking structure 14, effectively defining spaced channel pockets, wherein spacers 50 obviate blocking structure 14 extending the full length of plate 12, and wherein each blocking structure operates within a fabricated individual channel pocket in the plate. Each blocking structure 14 also embodies its own spring-restoration properties. As suggested by FIG. 11, where a blocking structure 14 is confined within such a pocket, having both side walls and end walls, no retainer 40 or studs 16 need be employed at the blocking structure. Namely, side walls 30, and end walls, of the pocket suitably retain the blocking structure from longitudinal and transverse movement with respect to the plate and pocket, and suitable top 34 and/or bottom 28 wall structure in the pocket prevent upward and downward movement of the blocking structure with respect to the pocket.

If desired, some interfering element other than the head of the screw can be used to activate and release the band. For example, an interfering element (not shown) can be designed into the screw below the screw head, above the screw head, or otherwise, for the purpose of activating movement and release of the band.

Whatever the positions of the bands, whatever the interfering element on the screw, which interfaces with the band, once the band is released from the movement caused by the respective interfering element, and the band thus returns to the position which it occupied prior to having been moved, the band is positioned above, over, and in an interfering and blocking abutment position with respect to a path which some portion of the screw must traverse in order to withdraw from the spinal plate assembly. Referring to FIG. 9B wherein the head of the screw has passed below the bottom of the band, and wherein the band has thus returned to the pre-stressed position, the band is seen to overlie a portion of the surface of the head of the screw, such that if the screw begins to withdraw e.g. away from the plate, the head of the screw impacts the bottom of the band. As withdrawal of the screw progresses such that the screw impacts the bottom of the band, the band, being supported by overhanging top walls 34, prevents the screw from further withdrawal from the plate.

As seen in FIG. 9A, when the screw is driven through the plate, e.g. and into bone material of a recipient user of the spinal plate assembly, the force applied by the upwardly-extending angular bottom surface of the screw automatically pushes the band aside as the head of the screw pushes against and passes the band. Once the head of the screw passes the band, the band is automatically restored to the unmoved position over the head of the screw, illustrated in FIG. 9B. Thus, in spinal plate assemblies of the invention, driving the bone screw, and thereby mounting the spinal plate assembly in the body of a recipient user thereof, automatically moves, optionally flexes, the band, as a blocking member, out of the way of insertion of the bone screw, and then the blocking member/band automatically moves to a blocking, locking position over the head or other control structure of the screw, thereby automatically activating the blocking and locking feature of the spinal plate assembly to block withdrawal of the bone screw, and thus to lock the bone screw in the assembly and retain joinder of the bone screw to the respective bone of the recipient user/patient. Such bone screw can, of course be released for removal by manually or otherwise intentionally moving or flexing the band away from the screw, and removing the screw while the band is thus held in the moved or flexed condition.

Figure 2:
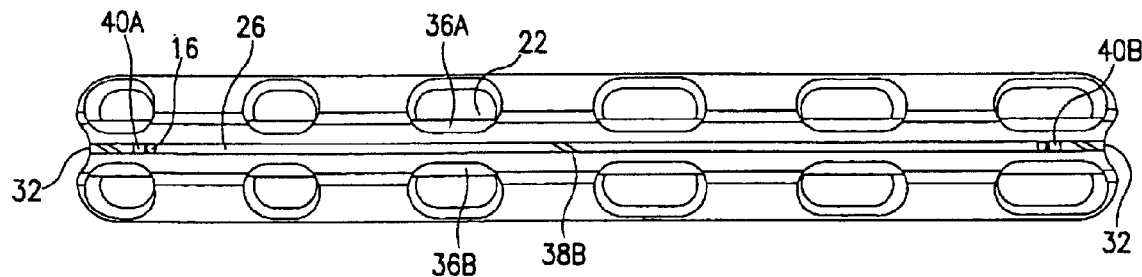
FIG. 2 shows a top view of the spinal plate assembly illustrated in FIG. 1.
Figure 4:
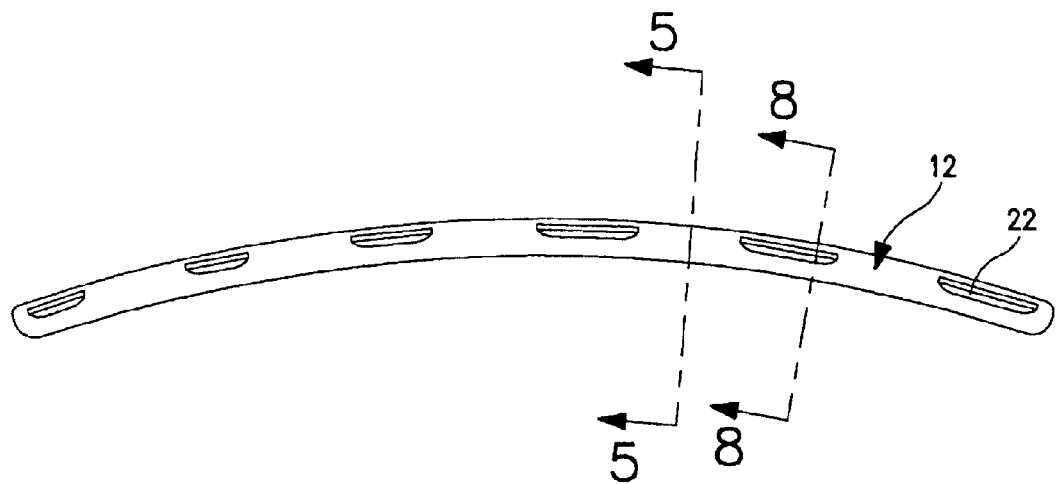
FIG. 4 shows a side view of the spinal plate assembly illustrated in FIG. 1.
Figure 3:
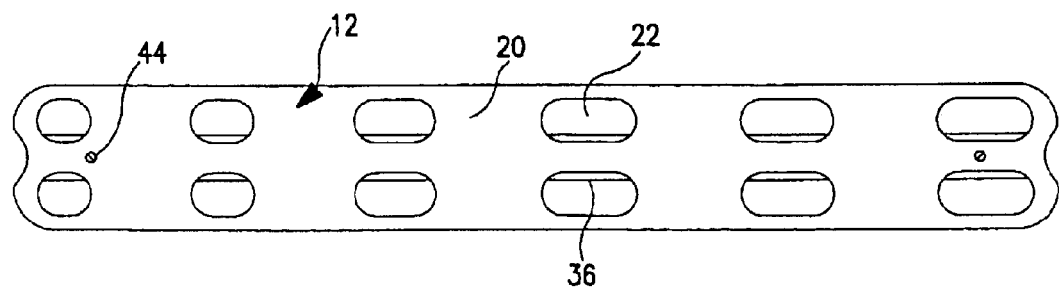
FIG. 3 shows a bottom view of the spinal plate assembly illustrated in FIG. 1.

In preferred embodiments of the invention, all of apertures 22 are slot-shaped in that, e.g. in projection, each aperture has an elongate dimension and a shorter cross-dimension. In some embodiments, two of the apertures are relatively lesser lengths, optionally circular, and serve as support apertures, and the remaining apertures are relatively greater lengths, as slots or slot-shaped, and serve as settle apertures, providing for the bone structure to settle while being advantageously held by the spinal plate. As seen in FIGS. 1 and 2, typically each aperture along the length of the spinal plate assembly can be progressively longer/shorter than the adjacent apertures in the same row, to accommodate the progressively increasing distance moved by respectively more upwardly-disposed ones of the vertebrae being treated by the plate assembly. All of the slots have commonly oriented axes along the elongate dimensions of the slots. Preferably, all apertures 22 are slot apertures having relatively longer lengths and relatively shorter widths.

Typical length increments for adjacent apertures are about 1 mm. Accordingly, in a plate 12 as in FIGS. 1–4 having 6 apertures per row, the length differential between the longest and shortest apertures 22 can be, for example, about 5 mm.

The exact and actual length differentials can be somewhat different, depending on the specific use contemplated for the respective plate 12.

Figure 12:
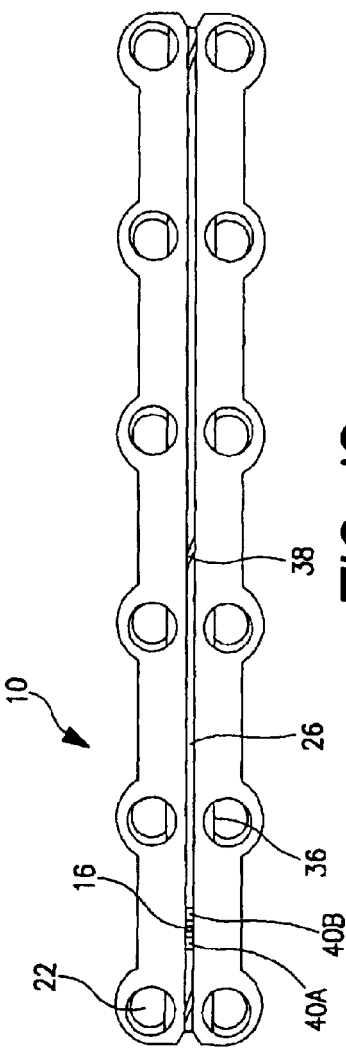
FIG. 12 shows a top view of a second family of embodiments of spinal plate assemblies as in FIGS. 1–4, and wherein all the bone-fastener-receiving apertures have substantially circular projected open areas.

FIG. 12 illustrates a spinal plate assembly 10 of the invention wherein all the bone screw apertures 22 are circular. Accordingly, the assembly of FIG. 12 provides for fixed positioning of the bone being supported. Otherwise, all features of the spinal plate assembly of FIG. 12 are substantially the same as the elements and features of the assemblies of e.g. FIGS. 1–11. Thus, bands 36 and springs 38 all employ the same principles illustrated hereinabove.

Typically, spinal plate assemblies of the invention have two rows of apertures 22. And while the spinal plate assemblies illustrated in the drawings show 2 rows of bone screw apertures, the invention can well be utilized with any desired number of rows of apertures, and any desired number of apertures per row, or any other arrangements of aperture array.

Those skilled in the art will now see that certain modifications can be made to the apparatus and methods herein disclosed with respect to the illustrated embodiments, without departing from the spirit of the instant invention. And while the invention has been described above with respect to the preferred embodiments, it will be understood that the invention is adapted to numerous rearrangements, modifications, and alterations, and all such arrangements, modifications, and alterations are intended to be within the scope of the appended claims.

To the extent the following claims use means plus function language, it is not meant to include there, or in the instant specification, anything not structurally equivalent to what is shown in the embodiments disclosed in the specification.

Having thus described the invention, what is claimed is:

1. Spinal plate structure, comprising:
   (a) a spinal plate having a bottom side generally adapted to face a plurality of vertebrae and a top side generally facing opposite the bottom side;
   (b) a plurality of bores defined by said spinal plate and passing through said spinal plate from the top side of said spinal plate to the bottom side of said spinal plate;
   (c) at least two bone anchors, each having a shank and a head, said head of each said bone anchor having a top surface, said at least two bone anchors being insertable into respective ones of the bores thereby to secure said spinal plate to such vertebrae; and
   (d) a retainer band adapted and configured to prevent bone anchor back-out, said retainer band being positioned within at least one of the bores and being confined between the top side and the bottom side of said spinal the plate, said the retainer band having
      (i) an initial position where at least a first portion of the length of said retainer band extends across a first portion of the respective bore,
      (ii) a passage position wherein the head of a said bone anchor which is being inserted into the respective bore has deflected said retainer band transversely relative to the respective bore up to a sufficient distance to accommodate passage of said head of the respective said bone anchor past said retainer band as said bone anchor is being driven to secure said plate to a respective such vertebra, and
      (iii) a retention position where such at least a first portion of the length of said retainer band again generally extends across such first portion of the respective bore and thereby is located proximal, and over, the respective bone anchor wherein said retainer band has a closed end portion which is stabilized relative to the top side and the bottom side of said spinal plate and has generally straight portions extending from the closed end portion and across at least a portion of the respective said bore.

2. Spinal plate structure as in claim 1 wherein said spinal plate has a generally arcuate shape.

3. Spinal plate structure as in claim 1 wherein the bores include first and second bores for attaching said spinal plate structure to a first such vertebra.

4. Spinal plate structure as in claim 1 wherein said spinal plate structure is sized and adapted to span at least two vertebrae, and at least one bore is provided for each such vertebra.

5. Spinal plate structure as in claim 4 wherein first such bores, in combination with first respective said bone anchors, prevent movement of said spinal plate relative to a first such vertebra, and wherein second such bores, in combination with second respective said bone anchors, accommodate movement of said spinal plate relative to a second such vertebra.

6. Spinal plate structure as in claim 5 wherein third such bores, in combination with third respective said bone anchors, accommodate movement of said spinal plate relative to a third such vertebra.

7. Spinal plate structure as in claim 4 wherein at least one such bore accommodates a said bone anchor secured therein, and secured to a such vertebra, translating within such bore.

8. Spinal plate structure as in claim 7 wherein such bores which accommodate anchors translating are elongated bores.

9. Spinal plate structure as in claim 1 wherein at least one such bore prevents a said anchor secured therein, and secured to a such vertebra, from translating within such bore and/or relative to said spinal plate.

10. Spinal plate structure as in claim 9 wherein such bores which prevent anchor translation are generally circular.

11. Spinal plate structure as in claim 1 wherein such bores include an interior surfaces and the interior surfaces at least in part define recesses which receive portions of the length of the respective said retainer band.

12. Spinal plate structure as in claim 11 wherein the recess in a given such bore generally defines a channel.

13. Spinal plate structure as in claim 11 wherein first and second ends of said retainer band are received in respective recesses in said spinal plate.

14. Spinal plate structure as in claim 1 wherein, when said bone anchors are in place, mounting said spinal plate to bone structure of a recipient user thereof, said retainer band, as associated with each said bone anchor, is positioned so as to be above the top surface of the respective said bone anchor.

15. Spinal plate structure as in claim 14 wherein said spinal plate includes a shoulder, proximate the bottom side of said spinal plate, in part defining the respective said bore for receiving said shank of the respective said bone anchor, said shoulder having an arcuate profile, said head of the respective said bone anchor having a bottom surface having an arcuate profile, said shank of the respective said bone anchor being smaller in cross-section than the respective said bore, said head of said bone anchor being larger than the respective bore at the shoulder of the bore, and the arcuate profile of the shoulder being complementary to the arcuate profile of the bottom surface of the head.

16. Spinal plate structure as in claim 1 wherein said head of a respective said bone anchor has a generally arcuate bottom surface, and the bottom surface interacts with a generally straight portion of said retainer band so as to function as a cam, thereby to move the retainer band from the initial position to the passage position and thus to enable said head to move, in the respective bore, sufficiently past said retainer band to enable said retainer band to move back toward the initial position and into the retention position, thus blocking withdrawal of said head of said bone anchor.

17. Spinal plate structure as in claim 16 wherein said retainer band moves to the retention position after said head of said bone anchor moves past said retainer band, a top surface of said bone anchor being configured so as to be unable to cam the respective portion of the length of said retainer band back to the passage position whereby said retainer band prevents anchor back-out.

18. Spinal plate structure as in claim 1 wherein said retainer band has a generally upwardly facing surface portion, a generally inwardly facing surface portion, and a joinder locus of said generally upwardly facing surface portion and said generally inwardly facing surface portion, and said head of said bone anchor contacts at least one of the generally upwardly facing surface portion, the generally inwardly facing surface portion, and the joinder locus, of said retainer band thereby to move said retainer band between the initial position and the passage position.

19. Spinal Plate structure as in claim 18 wherein said head of said bone anchor cams against at least one of the generally upwardly facing surface portion, the generally inwardly facing surface portion, and the joinder locus, of said retainer band thereby to move said retainer band between the initial position and the passage position.

20. Spinal plate structure as in claim 1 wherein said retainer band follows a continuous path and participates in defining an opening along the bore through which a respective said bone anchor passes as the respective said bone anchor secures said spinal plate to such vertebra.

21. Spinal plate structure as in claim 1, said retainer band at least in part defining a retainer, and wherein generally straight portions of said retainer extend between first and second ends thereof, and are generally parallel to each other in the initial position.

22. Spinal plate structure as in claim 1 wherein said retainer band is resiliently deflected into the passage position, and resiliently moves toward the retention position.

23. Spinal plate structure as in claim 1 wherein all of the bores are circular.

24. Spinal plate structure as in claim 1 wherein said retainer band has a closed end portion which is stabilized with respect to said spinal plate, and wherein generally straight-line portions of said retainer band extend across at least portions of respective ones of the bores.

25. Spinal plate structure, comprising:
(a) a spinal plate having first and second ends, a bottom side generally adapted to face a plurality of vertebrae, and a top side generally facing opposite the bottom side;
(b) a plurality of bores defined by said spinal plate and passing through said spinal plate from the top side of said spinal plate to the bottom side of said spinal plate;
(c) bone anchors, each having a shank and a head, said heads of said bone anchors having top surfaces, said bone anchors being insertable into respective ones of the bores thereby to secure said spinal plate to such vertebrae; and
(d) a retainer band defining first and second end portions generally directed toward the first and second ends of said spinal plate, said retainer band being adapted and configured to prevent bone anchor back-out, and being positioned within at least one of the bores,
a bore portion of the length of said retainer band extending, at an initial position, into and across a respective bore, at least a portion of the bore portion of said retainer band deviating from parallelism with an inwardly-facing side of the reactive bore,
at least one portion of said retainer band, between the first and second end portions of said retainer band, being resiliently deflectable in a direction transversely away from the respective bore, from an initial position to a passage position, thereby to enable a head of a said bone anchor to move into the bore and past said retainer band,
said retainer band being biased thereby to return toward the initial position after said head of said bone anchor has moved past said bore portion of said retainer band, whereby said retainer band extends across a portion of the respective bore and blocks back-out of said bone anchor.

26. Spinal plate structure as in claim 25 wherein said spinal plate has a generally arcuate shape.

27. Spinal plate structure as in claim 25 wherein said spinal plate structure is sized and adapted to span at least first and second vertebrae, and at least one such bore is provided for each such vertebra, wherein a first such bore, in combination with a first said bone anchor, prevents movement of said spinal plate relative to such first vertebra, and wherein a second such bore, in combination with a second said bone anchor, accommodates movement of said spinal plate relative to such second vertebra.

28. Spinal plate structure as in claim 27 wherein at least one such bore accommodates a said bone anchor secured therein, and secured to a such vertebra, translating within such bore.

29. Spinal plate structure as in claim 25 wherein at least one such bore prevents a said bone anchor secured therein, and secured to a such vertebra, from translating within such bore and/or relative to said spinal plate.

30. Spinal plate structure as in claim 29 wherein such bores which prevent anchor translation are generally circular.

31. Spinal plate structure as in claim 29 wherein such bores which accommodate anchors translating are elongate bores.

32. Spinal plate structure as in claim 25 wherein all of such bores are circular bores.

33. Spinal plate structure as in claim 25 wherein such bores include interior surfaces and the interior surfaces at least in part define recesses which receive at least a portion of the length of the respective said retainer band.

34. Spinal plate structure as in claim 33 wherein the recess in a given such bore generally defines a channel.

35. Spinal plate structure as in claim 25 wherein, when said bone anchors are in place, mounting said spinal plate to bone structure of a recipient user thereof, said retainer band, as associated with each said bone anchor, is positioned so as to be above the top surface of the respective said bone anchor.

36. Spinal plate structure as in claim 25 wherein said head of a respective said bone anchor has a generally arcuate bottom surface, and the bottom surface interacts with a generally straight portion of said retainer band so as to function as a cam, thereby to move the retainer band from the initial position to the passage position and thus to enable said head to move, in the respective bore, sufficiently past said retainer band to enable said retainer band to move back toward the initial position and into the retention position, thus blocking withdrawal of said head of said bone anchor.

37. Spinal plate structure as in claim 36 wherein said retainer band moves to the retention position after said head of said bone anchor moves past said retainer band, a top surface of said bone anchor being configured so as to be unable to cam the respective portion of the length of said retainer band back to the passage position, whereby said retainer band prevents anchor back-out.

38. Spinal plate structure as in claim 25 wherein said retainer band has a generally upwardly-facing surface portion, a generally inwardly-facing surface portion, and a joinder locus of said generally upwardly facing surface portion and said generally inwardly facing surface portion, and wherein said head of said bone anchor cams against at least one of the generally upwardly facing surface portion, the generally inwardly facing surface portion, and the joinder locus, of said retainer band thereby to move said retainer band between the initial position and the passage position.

39. Spinal plate structure as in claim 25 wherein all of the bores are circular.

40. A spinal plate assembly, comprising:
  (a) a spinal plate, said spinal plate comprising a top surface, a bottom surface opposite the top surface, the bottom surface being adapted and configured to be positioned adjacent a plurality of vertebrae of a recipient user, and a plurality of bone-fastener-receiving apertures which pass through said spinal plate from the top surface to the bottom surface, as to each such bone-fastener-receiving aperture, said spinal plate defining a projected outer perimeter extending about an aperture body;
  (b) a channel defined in and extending downwardly from the top surface of said spinal plate; and
  (c) a retainer band in said channel, said retainer band having a length, a width, and a height, a first portion of the length of said retainer band extending
    (i) at a first locus, across the projected outer perimeter and into the body, of at least one of the bone-fastener-receiving apertures,
    (ii) from the first locus, across a portion of the aperture body, and
    (iii) at a second locus, displaced from the first locus, back across the projected outer perimeter and off the body of the respective bone-fastener-receiving aperture,
    and from the second locus, an entirety of the width of a second portion of the length of said retainer band extends into the channel in said spinal plate such that material of said spinal plate is disposed between the top surface of said spinal plate and the entirety of the width of the second portion of the length of said retainer band.

41. A spinal plate assembly as in claim 40 wherein said retainer band is under constant compressive forces when so assembled to said spinal plate.

42. A spinal plate assembly as in claim 41 wherein said retainer band so extends across a first such bone-fastener-receiving aperture, and also extends across a second such bone-fastener-receiving aperture.

43. A spinal plate assembly as in claim 40 wherein a straight section of said retainer band extends generally uninterrupted from the first locus to the second locus.

44. A spinal plate assembly as in claim 43 wherein said retainer band so extends across a first such bone-fastener-receiving aperture, and also extends across a second such bone-fastener-receiving aperture.

45. A spinal plate assembly as in claim 40 wherein said retainer band so extends across a first such bone-fastener-receiving aperture, and also extends across a second such bone-fastener-receiving aperture.

46. Spinal plate structure as in claim 40 wherein first such bores, in combination with first respective said bone anchors, prevent movement of said spinal plate relative to a first such vertebra, and wherein second such bores, in combination with second respective said bone anchors, accommodate movement of said spinal plate relative to a second such vertebra.

47. Spinal plate structure as in claim 46 wherein third such bores, in combination with third respective said bone anchors, accommodate movement of said spinal plate relative to a third such vertebra.

48. Spinal plate structure as in claim 40 wherein at least one such bore accommodates a said bone anchor secured therein, and secured to a such vertebra, translating within such bore.

49. Spinal plate structure as in claim 40 wherein such bores include interior surfaces and the interior surfaces at least in part define recesses which receive portions of the length of the respective said retainer band.

50. Spinal plate structure as in claim 40 wherein first and second ends of said retainer band are received in respective recesses in said spinal plate.

51. Spinal plate structure as in claim 40 wherein, when said bone anchors are in place, mounting said spinal plate to bone structure of a recipient user thereof, said retainer band, as associated with each said bone anchor, is positioned so as to be above the top surface of the respective said bone anchor.

52. Spinal plate structure as in claim 40 wherein said head of a respective said bone anchor has a generally arcuate bottom surface, and the bottom surface interacts with a generally straight portion of said retainer band so as to function as a cam, thereby to move the retainer band from the initial position to the passage position and thus to enable said head to move, in the respective bore, sufficiently past said retainer band to enable said retainer band to move back toward the initial position and into the retention position, thus blocking withdrawal of said head of said bone anchor.

53. Spinal plate structure as in claim 52 wherein said retainer band moves to the retention position after said head of said bone anchor moves past said retainer band, a top surface of said bone anchor being configured so as to be unable to cam the respective portion of the length of said retainer band back to the passage position whereby said retainer band prevents anchor back-out.

54. Spinal plate structure as in claim 40 wherein said retainer band follows a continuous path and participates in defining an opening along the bore through which a respective said bone anchor passes as the respective said bone anchor secures said spinal plate to such vertebra.

55. Spinal plate structure as in claim 40, said retainer band at least in part defining a retainer, and wherein generally straight portions of said retainer band extend between first and second ends thereof, and are generally parallel to each other in the initial position.

56. Spinal plate structure as in claim 40 wherein said retainer band is resiliently deflected into the passage position, and resiliently moves toward the retention position.

57. Spinal plate structure as in claim 40 wherein all of the bore-fastener-receiving apertures are circular.

58. Spinal plate structure, comprising:
  (a) a spinal plate, said spinal plate comprising a top surface, a bottom surface opposite the top surface, the bottom surface being adapted and configured to be positioned adjacent vertebrae of a recipient user, and a plurality of bone-fastener-receiving apertures which pass through said spinal plate from the top surface to the bottom surface;

as to each such bone-fastener-receiving aperture, said spinal plate defining a projected outer perimeter extending about an aperture body;

(b) at least first and second bone fasteners, each having a head, said head of each said bone fastener having a top surface, said at least first and second bone anchors being insertable into respective ones of the bone-fastener-receiving aperture thereby to secure said spinal plate to such vertebrae; and (c) a retainer band having a length, and being adapted and configured to prevent bone anchor back-out, said retainer band extending across at least one of the bone-fastener-receiving aperture, said retainer band having (i) an initial position where at least a first generally straight-line portion of an inwardly-directed edge of said retainer band extends across a first portion of the respective bone-fastener-receiving aperture in a straight-line direction which is generally in common with a portion of the top surface of said plate, (ii) a passage position where the head of said bone anchor which is being inserted into the respective bone-fastener-receiving aperture has deflected said retainer band transversely relative to the respective bore up to a sufficient distance to accommodate passage of said head of the respective said bone anchor past said retainer band as said bone anchor is being driven to secure said plate to a respective such vertebra, and (iii) a retention position where such at least a first portion of the length of said retainer band again generally extends across such first portion of the respective bone-fastener-receiving aperture and thereby is located proximal, and over, a top surface of the head of the respective bone anchor.

59. Spinal plate structure as in claim 58 wherein first such bone-fastener-receiving apertures, in combination with first said bone fasteners, prevent movement of said spinal plate relative to a first such vertebra, and wherein second such bone-fastener-receiving apertures, in combination with second such bone fasteners, accommodate movement of said spinal plate relative to a second such vertebra.

60. Spinal plate structure as in claim 59 wherein third such bone-fastener-receiving apertures, in combination with third bone fasteners, accommodate movement of said spinal plate relative to a third such vertebra.

61. Spinal plate structure as in claim 58 wherein at least one such bone-fastener-receiving apertures, in combination with a said bone fastener, accommodates said bone fastener secured therein, and secured to a such vertebra, translating within such bone-fastener-receiving aperture.

62. Spinal plate structure as in claim 61 wherein such bone-fastener-receiving apertures which accommodate bone fastener translating are elongated bores.

63. Spinal plate structure as in claim 58 wherein at least one such bone-fastener-receiving aperture, in combination with a said bone fastener, prevents said bone fastener secured therein, and secured to a such vertebra, from translating within such bone-fastener-receiving aperture and/or relative to said spinal plate.

64. Spinal plate structure as in claim 63 wherein such bone-fastener-receiving apertures which prevent bone fastener translation are generally circular.

65. Spinal plate structure as in claim 58 wherein such bone-fastener-receiving apertures include interior surfaces and the interior surfaces at least in part define recesses which receive portions of the length of the respective said retainer band.

66. Spinal plate structure as in claim 65 wherein the recess in a given such bone-fastener-receiving aperture generally defines a channel.

67. Spinal plate structure as in claim 58 wherein first and second ends of said retainer band are received in respective recesses in said spinal plate.

68. Spinal plate structure as in claim 58 wherein, when said bone fasteners are in place, mounting said spinal plate to bone structure of a recipient user thereof, said retainer band associated with each said bone anchor is positioned so as to be above the top surface of the respective said bone fastener.

69. Spinal plate structure as in claim 58 wherein said retainer band is resiliently deflected into the passage position, and resiliently moves toward the retention position.

70. Spinal plate structure, comprising:
(a) a spinal plate, said spinal plate comprising a top surface, a bottom surface opposite the top surface, the bottom surface being adapted and configured to be positioned adjacent vertebrae of a recipient user, and a plurality of bone-fastener-receiving apertures which extend through said spinal plate from the top surface to the bottom surface;
(b) bone fasteners, each having a head; and
(c) a retainer band adapted and configured to prevent bone anchor back-out, said retainer band being positioned within at least one of the bores, said retainer band having first and second ends facing away from each other, and having
(i) an initial position where at least a first portion of said retainer band extends across a first portion of a respective bone-fastener-receiving aperture,
(ii) a passage position wherein the head of a said bone fastener which is being inserted into the respective bone-fastener-receiving aperture has deflected said retainer band transversely relative to the respective bone-fastener-receiving aperture up to a sufficient distance to accommodate passage of said head of the respective said bone fastener past said retainer band as said bone fastener is being driven to secure said plate to a respective such vertebra, and
(iii) a retention position where such at least a first portion of said retainer band again generally extends across such first portion of the respective bone-fastener-receiving aperture and thereby is located proximal, and over, the respective bone fastener.

71. Spinal plate structure as in claim 70 wherein first such bone-fastener-receiving apertures, in combination with first said bone fasteners, prevent movement of said spinal plate relative to a first such vertebra, and wherein second such bone-fastener-receiving apertures, in combination with second bone fasteners, accommodate movement of said spinal plate relative to a second such vertebra.

72. Spinal plate structure as in claim 71 wherein third such bone-fastener-receiving apertures, in combination with third said bone fasteners, accommodate movement of said spinal plate relative to a third such vertebra.

73. Spinal plate structure as in claim 70 wherein at least one such bone-fastener-receiving aperture, in combination with a said bone fastener, accommodates a said bone fastener secured therein, and secured to a such vertebra, translating within such bone-fastener-receiving aperture.

74. Spinal plate structure as in claim 70 wherein at least one such bone-fastener-receiving aperture, in combination with a said bone fastener, prevents said bone fastener secured therein, and secured to a such vertebra, from translating within such bone-fastener-receiving aperture and/or relative to said spinal plate.

75. Spinal plate structure as in claim 74 wherein such bone-fastener-receiving apertures preventing anchor translation are generally circular.

76. Spinal plate structure as in claim 75 wherein such bone-fastener-receiving apertures which accommodate anchors translating are elongated bores.

77. Spinal plate structure as in claim 70 wherein such bone-fastener-receiving apertures include interior surfaces and the interior surfaces at least in part define recesses which receive portions of the length of the respective said retainer band.

78. Spinal plate structure as in claim 77 wherein the recess in a given such bore generally defines a channel.

79. Spinal plate structure as in claim 70 wherein first and second ends of said retainer band are received in respective recesses in said spinal plate.

80. Spinal plate structure as in claim 70 wherein, when said bone fasteners are in place, mounting said spinal plate to bone structure of a recipient user thereof, said retainer band, as associated with each said bone anchor, is positioned so as to be above the top surface of the respective said bone fastener.

81. Spinal plate structure as in claim 70 wherein said retainer band is resiliently deflected into the passage position, and resiliently moves toward the retention position.

82. Spinal plate structure as in claim 70 wherein said retainer band has a closed end portion which is stabilized with respect to said spinal plate.

* * * * *